(12) United States Patent
Albala et al.

(10) Patent No.: US 11,666,728 B2
(45) Date of Patent: Jun. 6, 2023

(54) CIRCADIAN-FRIENDLY AND DISTANCE-RESPONSIVE LIGHTING SYSTEM

(71) Applicant: THOMAS JEFFERSON UNIVERSITY, Philadelphia, PA (US)

(72) Inventors: Lorenzo Albala, Philadelphia, PA (US); Graham Hale, Philadelphia, PA (US); Tim Bober, Philadelphia, PA (US); Bon Ku, Philadelphia, PA (US); Marcel Botha, New York, NY (US); Salih Berk Ilhan, Brooklyn, NY (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 742 days.

(21) Appl. No.: 16/321,804

(22) PCT Filed: Jul. 31, 2017

(86) PCT No.: PCT/US2017/044757
§ 371 (c)(1),
(2) Date: Jan. 29, 2019

(87) PCT Pub. No.: WO2018/023133
PCT Pub. Date: Feb. 1, 2018

(65) Prior Publication Data
US 2021/0275773 A1   Sep. 9, 2021

Related U.S. Application Data

(60) Provisional application No. 62/368,377, filed on Jul. 29, 2016.

(51) Int. Cl.
*A61M 21/02* (2006.01)
*H05B 47/115* (2020.01)
(Continued)

(52) U.S. Cl.
CPC .......... *A61M 21/02* (2013.01); *H04B 1/7163* (2013.01); *H04Q 9/00* (2013.01); *H05B 47/115* (2020.01);
(Continued)

(58) Field of Classification Search
CPC .......... A61M 21/02; A61M 2021/0044; A61M 2205/18; A61M 2205/3306;
(Continued)

(56) References Cited

U.S. PATENT DOCUMENTS

| 5,973,608 A | 10/1999 | McMahon |
| 6,816,086 B1 | 9/2004 | Kieffer |

(Continued)

FOREIGN PATENT DOCUMENTS

WO   2015113003 A1   6/2015

OTHER PUBLICATIONS

Alarifi, A.; Al-Salman, A.; Alsaleh, M.; Alnafessah, A.; Al-Hadhrami, S.; Al-Ammar, M.A.; Al-Khalifa, H.S. Ultra Wideband Indoor Positioning Technologies: Analysis and Recent Advances. Sensors 2016, 16, 707. https://doi.org/10.3390/s16050707 (Year: 2016).*

(Continued)

*Primary Examiner* — Sunita Reddy
(74) *Attorney, Agent, or Firm* — Cozen O'Connor

(57) ABSTRACT

A system to provide circadian-friendly lighting for nighttime hospital care comprising a lighting module and a transmitter tag that interface wirelessly wherein the lighting module comprises red-shifted light spectra, which is proven to be less disruptive to melatonin production than current blue-shifted hospital lighting; wherein the light output of the devices is modulated by the proximity of a tag to the device, with light intensity increasing with closer proximity between these two components and decreasing with increased dis- (Continued)

tance, thereby providing hands-free lighting to caregivers in the specific locations where they need light to perform care tasks.

4 Claims, 19 Drawing Sheets

(51) Int. Cl.

| | |
|---|---|
| *H05B 47/16* | (2020.01) |
| *H05B 47/175* | (2020.01) |
| *H05B 47/19* | (2020.01) |
| *H04B 1/7163* | (2011.01) |
| *H04Q 9/00* | (2006.01) |
| *A61M 21/00* | (2006.01) |

(52) U.S. Cl.
CPC .......... *H05B 47/16* (2020.01); *H05B 47/175* (2020.01); *H05B 47/19* (2020.01); *A61M 2021/0044* (2013.01); *A61M 2205/18* (2013.01); *A61M 2205/332* (2013.01); *A61M 2205/3306* (2013.01); *A61M 2205/3375* (2013.01); *A61M 2205/3592* (2013.01); *A61M 2205/8206* (2013.01); *H04B 2201/71634* (2013.01)

(58) Field of Classification Search
CPC .... A61M 2205/332; A61M 2205/3375; A61M 2205/3592; A61M 2205/8206; A61M 2205/3365; A61M 2205/3569; A61M 2230/63; H04B 1/7163; H04B 2201/71634; H04Q 9/00; H05B 47/115; H05B 47/16; H05B 47/175; H05B 47/19; H05B 47/12; G08C 17/02; G08C 2201/50; G08C 2201/91; F21W 2131/20; F21Y 2115/10; Y02B 20/40; A61N 5/0618; A61N 2005/0626; A61N 2005/0663; F21V 23/0471; F21V 21/0832; F21S 6/002
USPC ...................................................... 600/26–28
See application file for complete search history.

(56) References Cited

U.S. PATENT DOCUMENTS

| | | | | |
|---|---|---|---|---|
| 2004/0100376 | A1* | 5/2004 | Lye .................. | A61B 5/411 600/300 |
| 2005/0069726 | A1 | 3/2005 | Douglas et al. | |
| 2006/0181424 | A1* | 8/2006 | Graves ............... | G16H 40/20 600/300 |
| 2010/0277285 | A1* | 11/2010 | Anderson ........... | H04Q 9/00 340/10.4 |
| 2012/0206050 | A1* | 8/2012 | Spero ................. | F21V 19/02 315/152 |
| 2013/0165741 | A1* | 6/2013 | Seabury ............. | A61M 21/0094 600/27 |
| 2015/0048760 | A1* | 2/2015 | Kwag ................ | H05B 47/115 315/307 |
| 2015/0174361 | A1* | 6/2015 | Baaijens ............ | A61N 5/0618 600/27 |
| 2016/0212831 | A1 | 7/2016 | Dobai et al. | |
| 2016/0273717 | A1* | 9/2016 | Krames ............. | G02F 1/133603 |
| 2017/0080246 | A1* | 3/2017 | Knight .............. | A61G 10/02 |
| 2017/0105265 | A1* | 4/2017 | Sadwick ............ | H05B 47/11 |
| 2017/0105632 | A1* | 4/2017 | Chen ................ | H04N 7/183 |
| 2017/0189640 | A1* | 7/2017 | Sadwick ............ | H05B 45/20 |
| 2017/0238401 | A1* | 8/2017 | Sadwick ............ | H05B 45/10 315/294 |
| 2019/0191521 | A1* | 6/2019 | Kim ................. | H05B 47/19 |
| 2020/0178892 | A1* | 6/2020 | Maslik .............. | A61B 5/4836 |

OTHER PUBLICATIONS

Bedrosian, T.A., et al., "Influence of the modern light environment on mood", Molecular Psychiatry, vol. 18, No. 7, pp. 751-757, 2013.
Bourne, R.S., et al., "Melatonin: possible implications for the postoperative and critically ill patient", Intensive Care Medicine, vol. 32, No. 3, pp. 371-379, 2006.
Chellappa, S.L., et al., "Acute exposure to evening blue-enriched light impacts on human sleep", Journal of Sleep Research, vol. 22, No. 5, pp. 573-580, 2013.
Ely, E.W., et al., "Delirium as a predictor of mortality in mechanically ventilated patients in the intensive care unit", JAMA, vol. 291, No. 14, pp. 1753-1762, 2004.
Friese, R.S., et al., "Quantity and quality of sleep in the surgical intensive care unit: are our patients sleeping?, Journal of Trauma and Acute Care Surgery, vol. 63, No. 6, pp. 1210-1214, 2007.
Girard, T.D., et al., "Delirium as a predictor of long-term cognitive impairment in survivors of critical illness", Critical Care Medicine, vol. 38, No. 7, pp. 1513-1520, 2010.
International Search Report and Written Opinion dated Dec. 7, 2017 in International Application No. PCT/US2017/044757.
Kamdar, B.B., et al., "Perceptions and Practices Regarding Sleep in the ICU: A Survey of 1,223 Critical Care Providers", Annals of the American Thoracic Society, vol. 13, No. 8, pp. 1370-1377, 2016.
Koninklijke Philips Electronics N.V. Healwell—A New Lighting Solution for Patient Rooms, N.p.: Koninklijke Philips Electronics N.V. 2011, HealWell-Philips Lighting, Koninklijke Philips Electronics N.V., Dec. 2011, Web Apr. 29, 2016.
Leslie, D.L., et al., "The Importance of Delirium: Economic and Societal Costs", Journal of the American Geriatrics Society, vol. 59, Suppl. 2, pp. S241-S243, 2011, doi: 10.1111/j.1532-5415.2011.03671.x.
Milbrandt, E.B., et al., "Costs associated with delirium in mechanically ventilated patients", Crit Care Med., vol. 32, No. 4, pp. 955-962, 2004.
Rubin, F.H., et al., "Sustainability and scalability of the hospital elder life program at a community hospital", Journal of the American Geriatrics Society, vol. 59, No. 2, pp. 359-365, 2011.
Satlin, A., et al., "Bright light treatment of behavioral and sleep disturbances in patients with Alzheimer's disease", American Journal of Psychiatry, vol. 149, No. 8, pp. 1028-1032, 1992.
Thomason, J.W., et al., "Intensive care unit delirium is an independent predictor of longer hospital stay: a prospective analysis of 261 nonventilated patients", Crit Care, vol. 9, No. 4, pp. R375-R381, 2005.
Van Someren, et al., "Indirect bright light improves circadian rest-activity rhythm disturbances in dementia patients", Biological Psychiatry, vol. 41, No. 9, pp. 955-963, 1997.
Weinhouse, G.L., et al., "Bench-to-bedside review: delirium in ICU patients—importance of sleep deprivation", Crit Care, vol. 13, No. 6, pp. 234 (8 pages), 2009.

* cited by examiner

| INPUT | OUTPUT |
|---|---|
| Tag/user enters room | Light turns on; brightness is a function of proximity |
| Tag/user leaves room | Light turns off, fading to off as a function of proximity |
| Manually turning on light | Light turns on |

FIG. 12

CIRCADIAN-FRIENDLY AND DISTANCE-RESPONSIVE LIGHTING SYSTEM

CROSS REFERENCE TO RELATED APPLICATIONS

This application is a U.S. National Phase Stage of International Application No. PCT/US2017/044757, filed Jul. 31, 2017, which claims priority to U.S. Provisional Patent Application No. 62/368,377, filed Jul. 29, 2016, each of which are incorporated herein by reference in their entirety.

FIELD OF INVENTION

The present invention is generally related to lighting systems emanating circadian friendly wavelength light within a system that illuminates the lighting systems based on distance responsive technology.

BACKGROUND OF INVENTION

Sleep or lack thereof has profound effects on the human body, its ability to mount immune responses, and deal with stress. The body adapts to a lack of sleep by increasing production of stress mediators like cortisol and catecholamines, which increases heart rate and blood pressure. The effects of sleep deprivation are multifactorial—including a decreased ability of the body to fight infection, altered respiratory capability, increased proclivity towards diabetes, decreased ability to prevent and fight off cancer, and impaired mobilization after injury. Nighttime disruptions are also variable—including light, noise levels, patient care activities, mechanical ventilation techniques, and prescribed medications like benzodiazepines (Kamdar et al. 2016). Typically, the body regulates sleep through appropriate wake/sleep cycles based on circadian rhythm.

Circadian rhythms are a central part of human biology. In the absence of light, retinal photoreceptors in the eye stop signaling to deeper structures in the brain. Thus, darkness informs the body's ability to sleep via a substance called melatonin, which is produced in the brain. Blue-rich light (particularly shorter wavelengths, in the 460-480 nanometer wavelength range) is maximally effective at stimulating retinal photoreceptors in the eye, which, in turn, maximally disrupts the endogenous production of melatonin. In turn, the absence of this retinal signal allows the pineal gland (another deep structure in the brain) to produce melatonin. Light signals are the sole stimulus that directly suppresses melatonin to near-zero levels, functioning as a trigger for sleep-wake cycles. As soon as humans are in darkness, melatonin quickly increases, functioning as a trigger for sleep and a critical component of our diurnal biology.

The timing of lighting throughout a day is essential for the maintenance of circadian rhythms. When a healthcare provider turns on the light in a hospital room at night, the production of melatonin plummets—thereby limiting the body's natural mechanism to fall asleep, stay asleep, and have normal sleep architecture (Chellappa et Al, 2013). This results in repeated sleep interruptions, reduced time to fall asleep, and an overall unpleasant sleep experience leading to worsened mood and satisfaction (Bedrosian and Nelson, 2013). Impaired melatonin cycles have also been linked to psychoses in post-surgical patients (Bourne and Mills, 2006). Thus, the tactful application of light throughout a day can significantly impact the course of patient care.

LED and responsive lighting systems are becoming increasingly prevalent in modern hospital settings. Philips, a major company in the lighting industry, has developed the "HEALWELL" lighting system, which redesigns the layout of entire hospital rooms with adaptive lighting that is responsive to the preferences of patients and providers throughout the day. On a smaller scale, LED-based interventions like IV illuminators frequently used to monitor the flow of fluids in operating rooms and patient rooms, although they are not "circadian-friendly" and have very limited flexibility in providing light where providers need it most. The issues with these current interventions is that they are either too limited to accommodate the full scope of nighttime care (i.e. low-cost IV illuminators) or too expensive to adopt throughout the hospital (i.e. the Philips HealWell system).

Sleep deprivation is physiologically and psychologically damaging to patients and their healing. Hospital care often requires attention to the patient during a full 24-hour period, including blood draws, IV bag changes, tests being completed, and simple status checks that are mandated by law, regardless of whether it is 3:00 AM or 3:00 PM. The use of inappropriate, non-circadian-friendly lighting throughout the night is a physiologic disruptor that translates to perceived poor quality sleep. To this end, surveyed hospital patients rank sleep deprivation as their third greatest fear—only after pain and intubation (Kamdar et al. 2016).

Many studies have demonstrated the impact of sleep hygiene on patient healing. A recent survey of 1,223 nurses and physicians in 24 countries worldwide found that 88% said that poor sleep could negatively affect the quality of healing and could contribute to longer length of stay, poor participation in physical therapy, and delayed weaning off of mechanical ventilators (Kamdar et al. 2016). Constant light disruptions during the night harm the normal architecture of patient sleep, as evidenced by a polysomnography study of ICU patients that demonstrated that, though they got 8 hours of sleep per day, patient spent more time in the superficial (and less restful) stages (Friese et al. 2007). Poor sleep quality is linked to several psychological disturbances including delirium (i.e. an acute decline in cognitive ability), which commonly manifests in hospitalized patients. Delirium itself has been tied to increased length of stay, cost, cognitive impairment, and mortality in the ICU setting and is believed to account for $143-152 billion in healthcare expenditures each year (Leslie et al. 2011).

The responsive lighting system of the present disclosure seeks to intervene at this *nexus*—the 24-hour nature of patient care coupled with the necessity of sleep as part of the healing process.

SUMMARY OF INVENTION

The present disclosure represents a method for a system of automatically activated, task-based lighting designed to be minimally disruptive to overnight melatonin production in humans. This suite of LED-equipped lighting products provide a low-cost, biologically-informed, environmentally-responsive lighting system that enables caregivers to do their jobs without disrupting patient sleep, hospital workflow, or patient room infrastructure.

The system described herein is intended to provide a cost-effective option to provide circadian-friendly lighting for nighttime hospital care. The selected LED technology for the lighting system of the present disclosure features red-shifted light emission spectrum, which is proven to be less disruptive to melatonin production than current blue-shifted hospital lighting. The light output of the devices is modulated by the proximity of a transmitter tag (worn by the provider) to the device, with light intensity increasing with closer proximity between these two components and decreasing with increased distance. The lighting devices are small modular units that can be attached to railings and fixtures throughout the hospital room—thereby providing hands-free lighting to caregivers in the specific locations where they need light to perform care tasks. We anticipate future applications of this technology in other care settings, such as long-term nursing care, assisted living facilities, and even in the home (e.g. children's rooms).

In a preferred embodiment is described a system to provide circadian-friendly lighting for nighttime hospital care comprising a lighting module anchor, a sensing mechanism, and a processor, wherein the lighting module comprises red-shifted light spectra; wherein the light output of the devices is modulated by the proximity of a sensor to the device, with light intensity increasing with closer proximity between these two components and decreasing with increased distance, thereby providing hands-free lighting to caregivers in the specific locations where they need light to perform care tasks. In certain embodiments, the lighting module anchor comprises a sensor selected from the group consisting of a light, sound, vibration, rotation sensor, or combinations thereof. In certain embodiments, the lighting module anchor and the sensing mechanism determine proximity through UWB telemetry. In preferred embodiments, the lighting module anchor comprises a battery, a sensor, at least one LED in the red-shifted light spectra, and UWB telemetry to communicate wirelessly with a paired sensing mechanism. In preferred embodiments, the red-shifted light spectra reduces light in the 460-480 nanometer wavelength range.

In preferred embodiments, a system functions based on a distance between the anchor and a sensing mechanism (tag), wherein proximity between the anchor and the sensing mechanism of 8 feet illuminates the lighting module anchor, and a distance of 1 feet or less increases the light to 100% intensity. The particular distances of 8 feet and 1 foot can be modified based on the needs of the particular application to nearly any distance.

A method of illuminating a location with a red-shifted light spectra comprising a system to provide circadian-friendly lighting comprising a lighting module anchor, a sensor mechanism, and a processor, wherein the lighting module anchor comprises red-shifted light spectra; wherein the light output of the module is modulated by the proximity of a sensor to the device, with light intensity increasing with closer proximity between these two components and decreasing with increased distance, thereby providing hands-free lighting to a location; wherein the method comprises the steps of: engaging a red-shifted light module with a sensor; increasing the intensity of the red-shifted light upon increase of proximity to the sensor; decreasing the intensity of the red-shifted light upon reduction of the proximity to the sensor. In preferred embodiments, the lighting module anchor comprises a sensor selected from the group consisting of a light, sound, vibration, rotation sensor, or combinations thereof. In preferred embodiments, the lighting module anchor and the sensing mechanism determine proximity through UWB telemetry.

In preferred embodiments, a lighting module anchor comprises a battery, a sensor, at least one LED in the red-shifted light spectra, and UWB telemetry to communicate wirelessly with a paired sensing mechanism. Preferably, the red-shifted light spectra reduces light in the 460-480 nanometer wavelength range.

A method for illuminating a space comprising a lighting module, a null pressure sensor, and an alarm mechanism; indicating a force on the null pressure sensor which turns off the lighting module; releasing pressure from the null pressure system wherein the lighting module is illuminated; turning off the light upon re-application of a force on the null pressure sensor. In certain embodiments, the alarm mechanism is generated, so as to identify that the lighting module has illuminated. In certain embodiments, the method utilizes a timer, wherein a timer begins counting down upon a release of pressure from the null pressure system and the alarm mechanism is generated only upon the timer reaching a pre-determined time.

In a further embodiment, a user-responsive lighting system that employs a distance-based stimulus to turn on the light via wireless communication comprising a lighting module anchor and a wireless communication tag; said lighting module anchor comprising a light, a battery, a processor, a wireless communication module, and a sensor; and said wireless communication tag comprising a wireless communication component having connectivity means to said wireless connectivity module of said lighting module anchor; wherein said wireless communication allows for automatic, distance-based long-wavelength illumination of areas of interest; wherein a light is illuminated upon proximity between said lighting module anchor and said wireless communication tag of at least 8 feet, and wherein the intensity of the light increases as the proximity between the lighting module anchor and the wireless communication tag decreases; and wherein the light is off when the proximity is more than 8 feet. In certain embodiments, said lighting module anchor further comprises a light sensor which prevents illumination of the light when the sensor is activated by another light source. In certain embodiments, said lighting module anchor further comprises a sound sensor for an added activation mode, responsive to loud and protracted audio cues. In certain embodiments, wireless communication is selected from the group consisting of: UWB, Bluetooth, 434 Mhz radio, and combinations thereof.

A further embodiment is A method of activating a light source comprising placing a light anchor within wireless communication of a tag, wherein the light source anchors are sensitive to binary on/off cues, and wherein tags are equipped with on/off physical toggle, and can be placed anywhere in the range of the wireless transmission to anchor, and said tags comprising a small magnet within the tag, allowing for versatile placement anywhere that a magnetic surface allows; activating said light source anchor by pressing a binary on/off cue on said tag.

A further embodiment is directed towards a method of activating an electronic switch through a wireless communication mechanism; comprising an electrical switch component comprising a wireless communication mechanism, and a processor; a wireless tag comprising a wireless communication component selected to engage with the wireless communication mechanism of said electrical switch component; wherein said electronic switch is activated between a first and second state based upon proximity between the electrical switch component and the wireless tag. In certain embodiments, the electrical switch component is selected from the group consisting of a light, an electrical outlet, or a motor relay.

A further embodiment is directed towards a method of identifying the location of a wireless tag in a system of anchor bases comprising; at least three anchor bases, said anchor bases comprising a power source, a processor, a wireless connection mechanism, memory; and at least one wireless tag, comprising a wireless connection component, a battery, and a processor, determining the relative position of the wireless tag between the at least three anchor bases wherein each anchor base senses the position of the wireless tag to orient the wireless tag in 3D, and communicating the relative positon of the tag based on the determination made between the at least three anchor bases.

A further embodiment is a system to provide circadian-friendly lighting for nighttime hospital care comprising a lighting module anchor comprising a processor, a light sensor, a sound sensor, and wireless telemetry, a sensing mechanism (tag) comprising wireless telemetry to communicate wirelessly with said lighting module anchor, wherein the lighting module comprises red-shifted light spectra; wherein the light output of the devices is modulated by the proximity of a sensor to the device, with light intensity increasing with closer proximity between these two components and decreasing with increased distance, thereby providing hands-free lighting to caregivers in the specific locations where they need light to perform care tasks, and wherein the light illuminates only when the light sensor identifies lack of light to the sensor; and further wherein the light will illuminate, absent the sensing mechanism upon a sound of greater than a predetermined decibel level for more than 5 seconds.

BRIEF DESCRIPTIONS OF THE FIGURES

FIG. 1 depicts a perspective view of a light anchor.
FIG. 2 depicts a front plan view of a light anchor.
FIG. 3 depicts a rear plan view of a light anchor.
FIG. 4 depicts a side plan view of a light anchor.
FIG. 5 depicts a side plan view of a light anchor.
FIG. 6 depicts a top perspective view of a light anchor.
FIG. 7 depicts a bottom perspective view of a light anchor.
FIG. 8 depicts a hanging light anchor in a first left image, an anchor placed on a surface, and communicating with a tag carried by a caregiver in the middle image, and depicts how the feet on the lighting module can stand on a curved or flat surface on the right most image.
FIG. 9 depicts an IV drip module anchor that is suitable for illuminating the IV drip line.
FIG. 10 depicts a flow-chart of a typical nurse/patient interaction with a standard light system and with the system as described herein.
FIG. 11 depicts an idea chart of issues from sleep disruption in an ICU patient.
FIG. 12 depicts a possible input and output for the system.
FIG. 13 depicts an anchor and proximate tags, depicting the light intensity based on distance between the tag and the anchor.
FIG. 14 depicts triangulation between a tag and three anchors.
FIG. 15 depicts a car passing by several light posts, wherein the lights illuminate based on the proximity of a vehicle with a tag.
FIG. 16 (top half) depicts a tag equipped with either a flashing LED or vibrating capability, which can serve as an alarm or notification; in other words, a device linked to the tag can notify the wearer of some trigger. A second version of this idea (bottom half): a physical device possessing an integrated tag (a UWB transmitter) can activate an anchor (UWB receiver), such as a circalight (anchor); so that e.g. a bed pressure sensor activated will cause simultaneous activation of a nearby anchor (circalight).

DETAILED DESCRIPTION OF THE EMBODIMENTS

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

Circadian-friendly (definition): A circadian rhythm is defined as a pattern based on a day/night cycle, especially the repetition of certain physiological phenomena, such as sleeping. A circadian-friendly device will be used during said occurrences without disrupting natural biochemistry.

Poor sleep is a common problem and caregivers in many industries, and at home, are challenged by the balance of necessary care tasks and quality of well-lit care activities. Indeed, circadian-friendly lights that are responsive to the distance of users can benefit users in a variety of scenarios: from care tasks in nursing home and long-term care facilities to consumer use in the context of infant night-time care to generally circadian-conscious individuals in all walks of life. Accordingly, the device and system described herein has applications in a variety of fields where illumination of certain aspects is either necessary, or helpfully provides general illumination or targeted illuminate to aid in task completion.

Presently, there are no solutions involving a distance-sensing tag and anchor (the light) combination that provide localized, portable, and circadian-friendly night-time light.

The device described herein represents a system of automatically activated, task-based, circadian-friendly lighting, featuring a suite of solutions to accommodate different lighting needs and scenarios.

Figure 1:
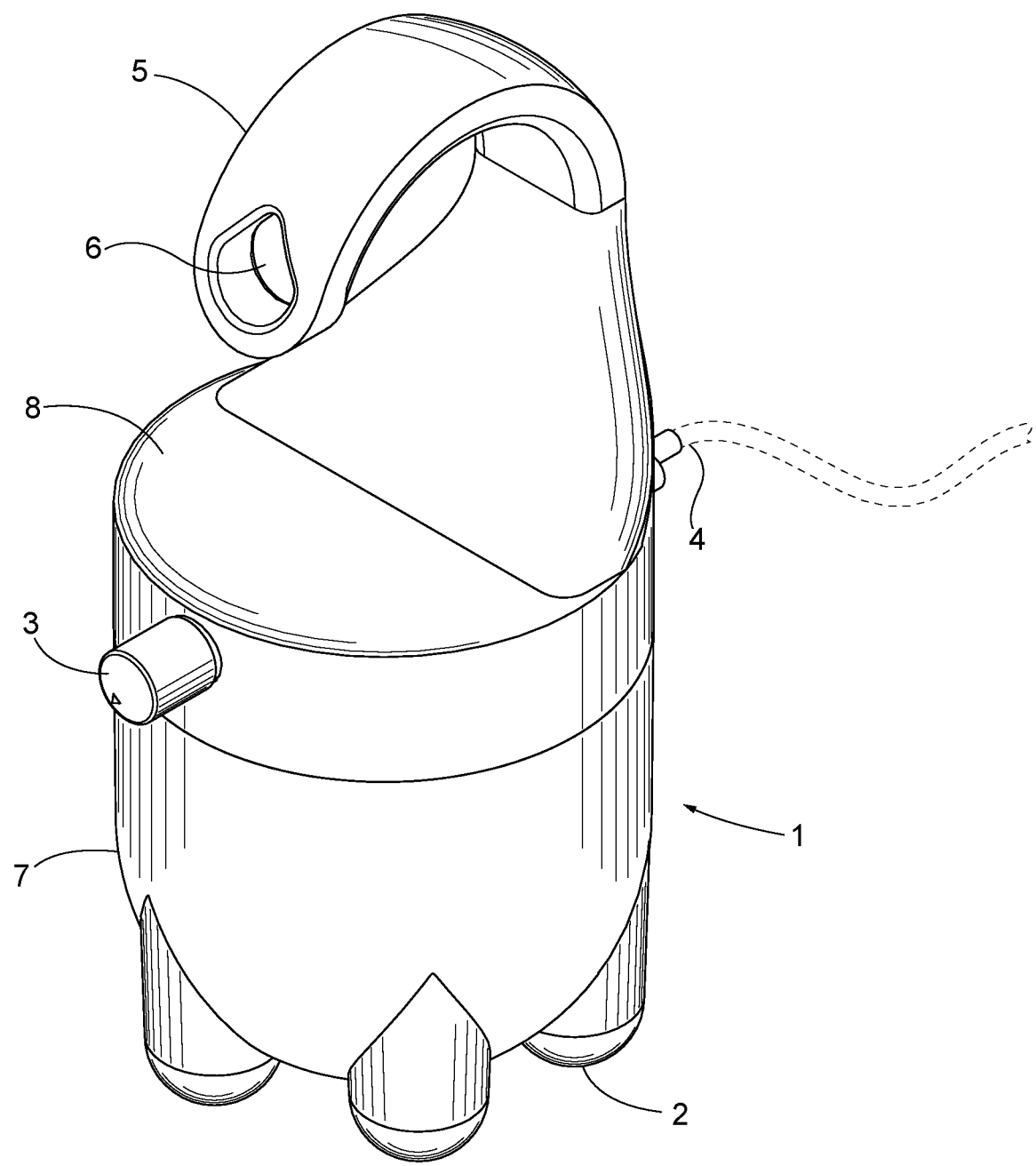

FIG. 1 depicts and anchor 1 having a base with feet 2, a body 7, a top 8, a knob 3, a neck 5, a neck opening 6, and a power cord. An anchor, as described throughout the specification is preferably combined with a tag 11 to allow for wireless activation of the anchor 1. The anchor comprises at least one light source within the body 7, for example a LED light. Other known light sources can be utilized as appropriate for the particular application of the anchor 1, however LED lights and their progeny are useful for their long life, lower power consumption, and generally low operating temperatures. These features are desirable for a light source.

Figure 8:
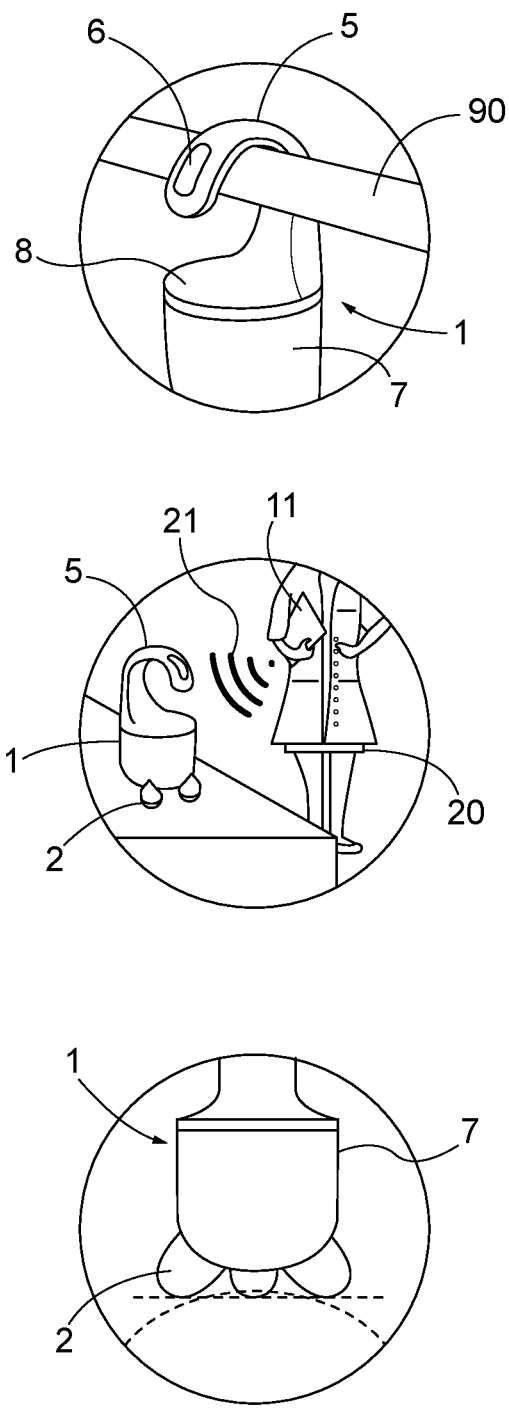

The feet 2 of the device are positioned to allow for secure placement on a flat surface, or on a round surface. These variations are shown in FIG. 8, which shows both a flat surface, in the middle image, and a rounded surface on the right image. The knob 3 is utilized as a control device to perform several tasks. First, the knob can indicate the intensity of light when at 100% or at any lower percentage. A turn can simple increase or decrease the desired intensity. Furthermore, the knob 3 can be used to turn the device from one mode to another. For example a binary mode of on/off, fully on, fully off, or relative intensity based on proximity to a tag. Additional uses of the knob can be modified based on the software utilized with the device as necessary to control additional sensors used on an anchor 1.

The top 8 and the body 7 are preferably translucent, but may include a tinted color as appropriate for the use and function. Alternatively, the top 8 may be opaque, while the body 7 is translucent or the top 8 may be translucent and the body 7 opaque. At least one must be translucent to allow for the internal light source (e.g. 70 in FIG. 18) to allow for light to shine through the material.

The neck 5 is curved to allow for easy hanging on a pole, a hook or the like. Indeed, a neck hole 6 is further included to allow for more secure placement on a hook, or on a nail or screw, or to allow for a tie or other material to secure the neck 5 to a particular location. For example, a lock or twist-tie may be tied through the neck opening 6 to secure the anchor 1 to a particular location.

Finally, a cord 4 is provided. This can be utilized to charge the anchor 1, or to power it directly, when direct power sources are available. A battery is included within the anchor 1, to allow for wireless illumination. Furthermore, this battery, when no power source is otherwise directly provided, powers the internal components and/or sensors that activate the anchor device.

Figure 2:
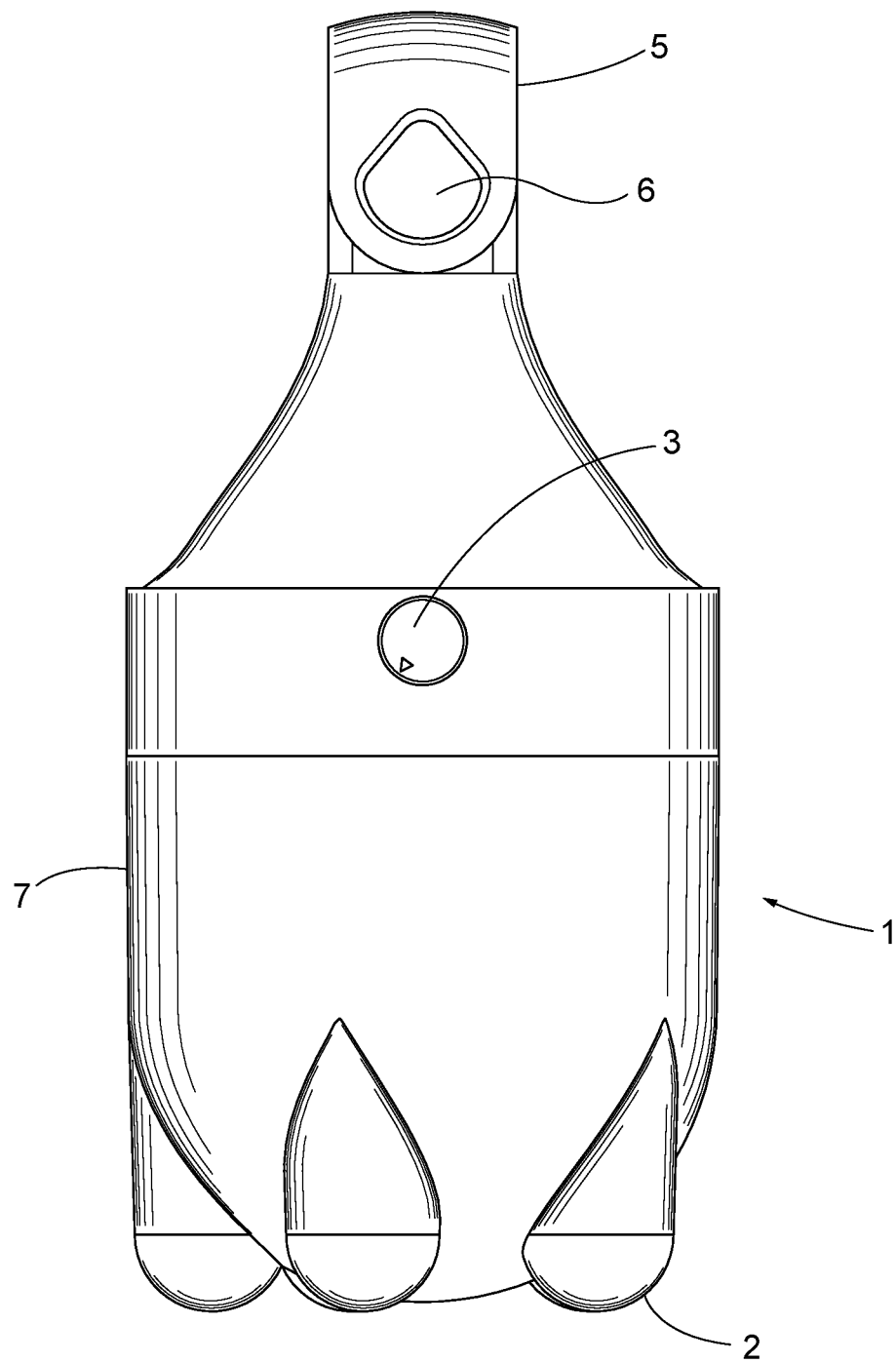

FIG. 2 provides a separate front view of the anchor 1.

Figure 3:
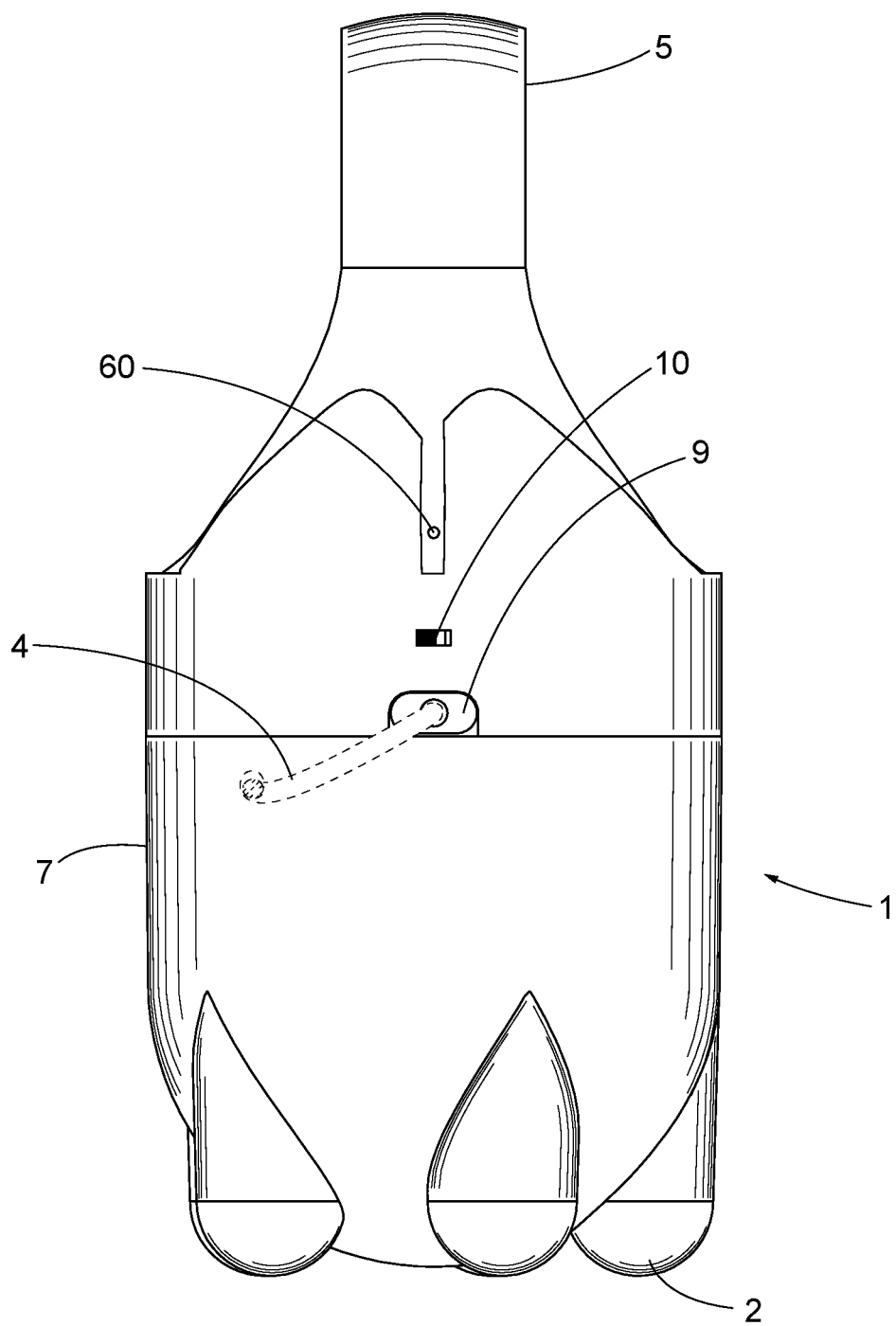

FIG. 3 provides a rear view of the anchor 1, and further defines a power plug 9, which connects the cord 4 to the anchor 1. Further depicted is a switch 10, which can be used for one or more features. For example, the switch can be an on/off/or mode switch, having three positions. Or can be a simple two mode switch, from on to off. The switch 10 can be used in conjunction with the knob 3 to control the actions of the anchor 1. A round sensor opening 60 is provided at the rear. This sensor 60 provides for external collection of data, where appropriate. However, internal collection by sensors is also provided and may be sufficient in certain embodiments. The sensor 60 may be connected to a light sensor, a sound sensor, or another sensor utilized with the device.

Figure 4:
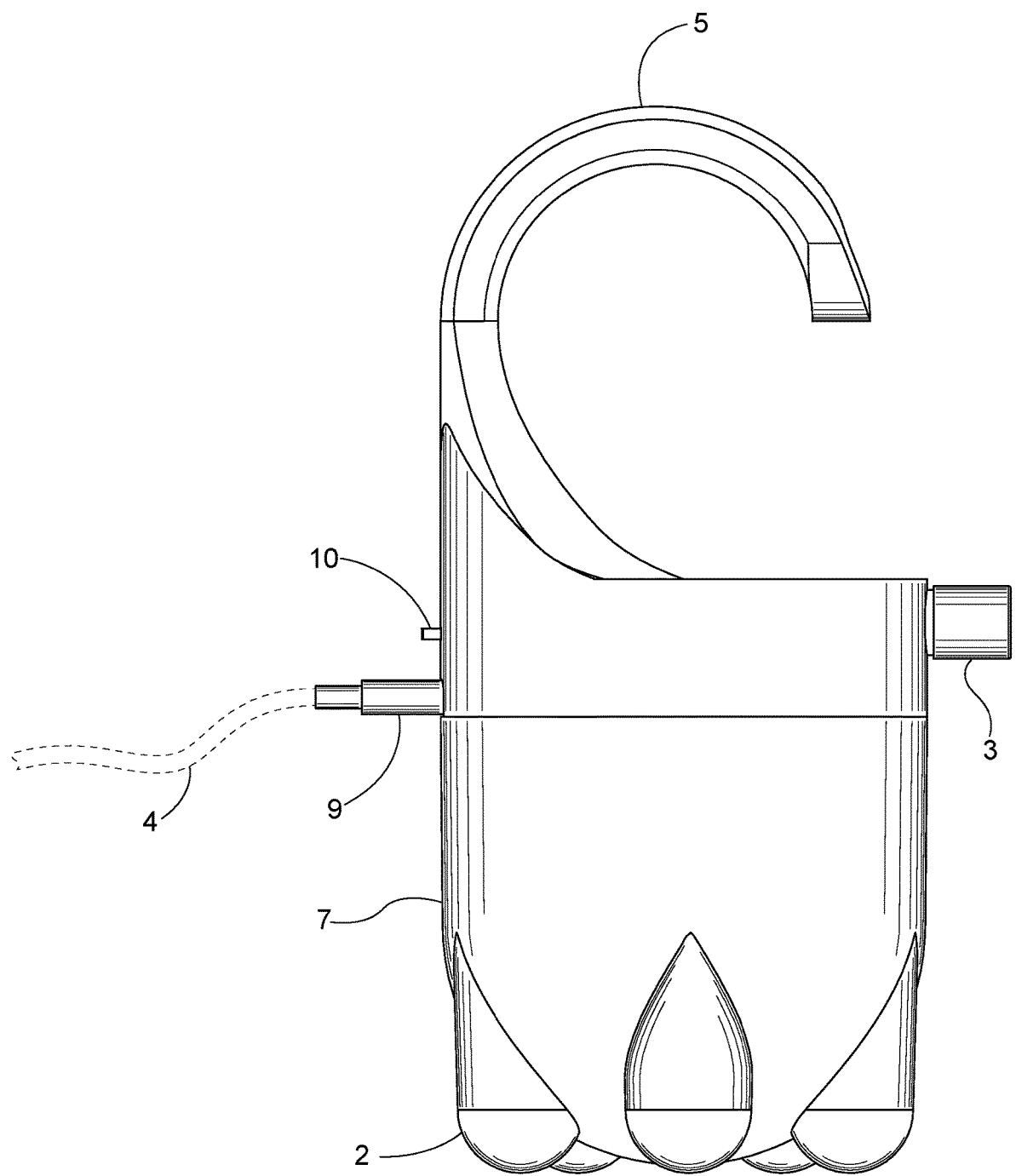
Figure 5:
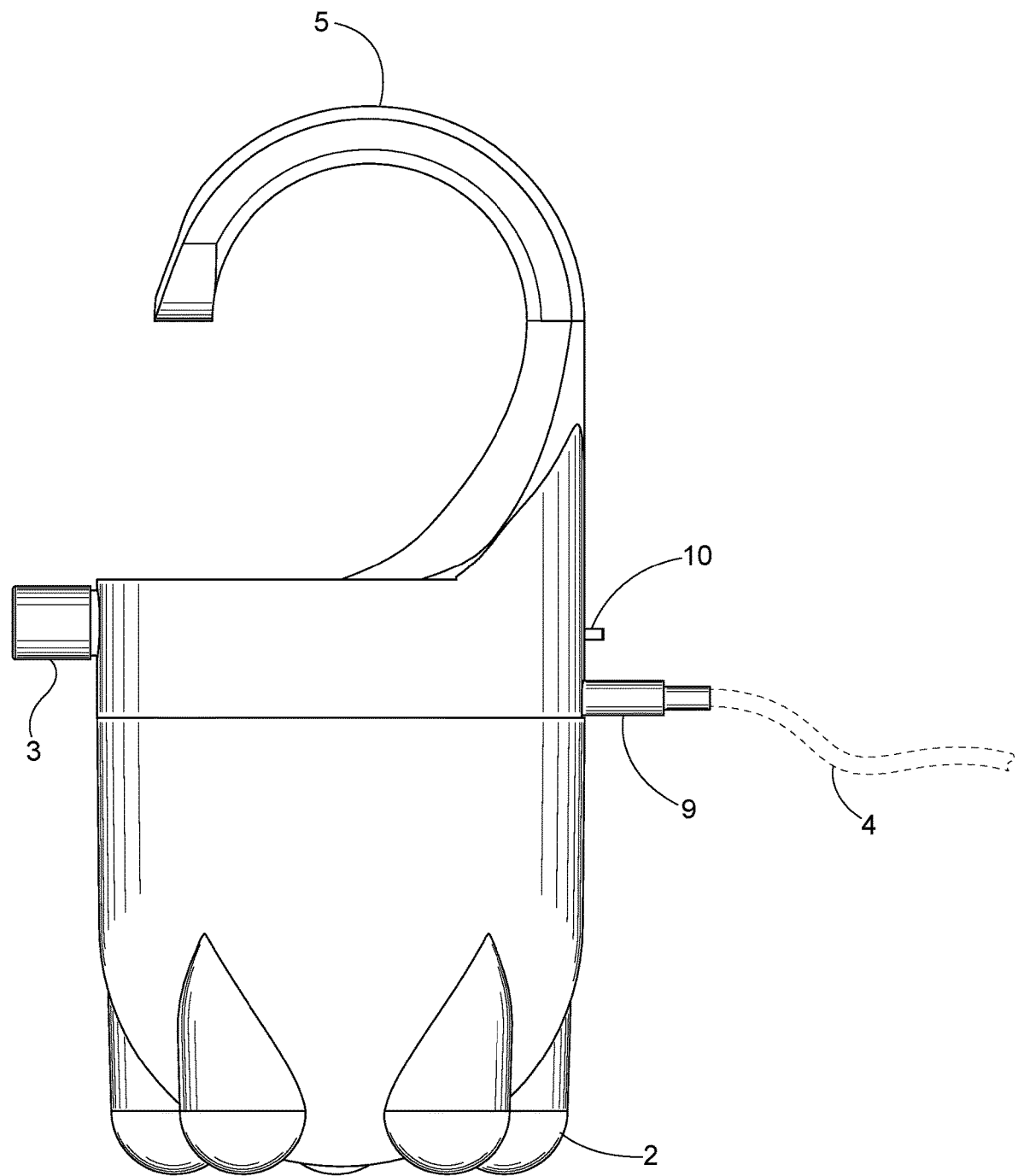

FIGS. 4 and 5 depict a left and right views of the anchor 1.

Figure 6:
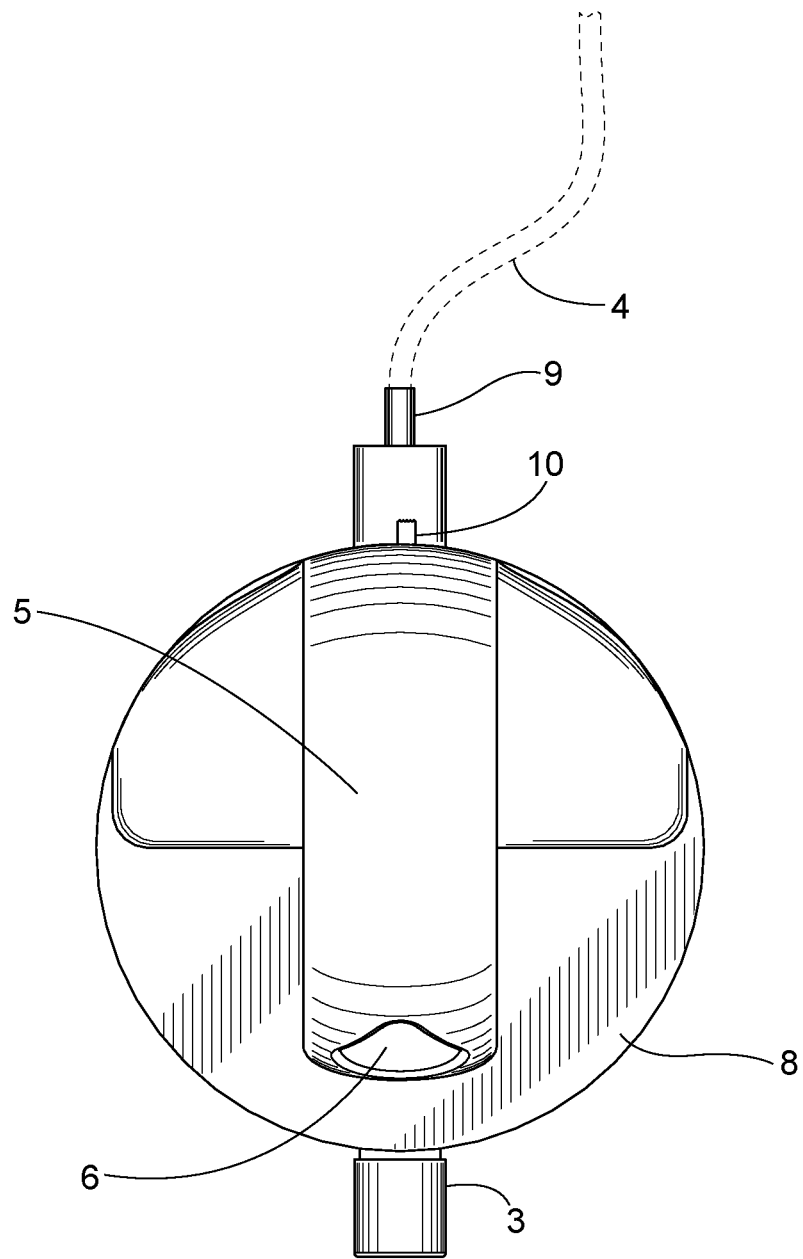
Figure 7:
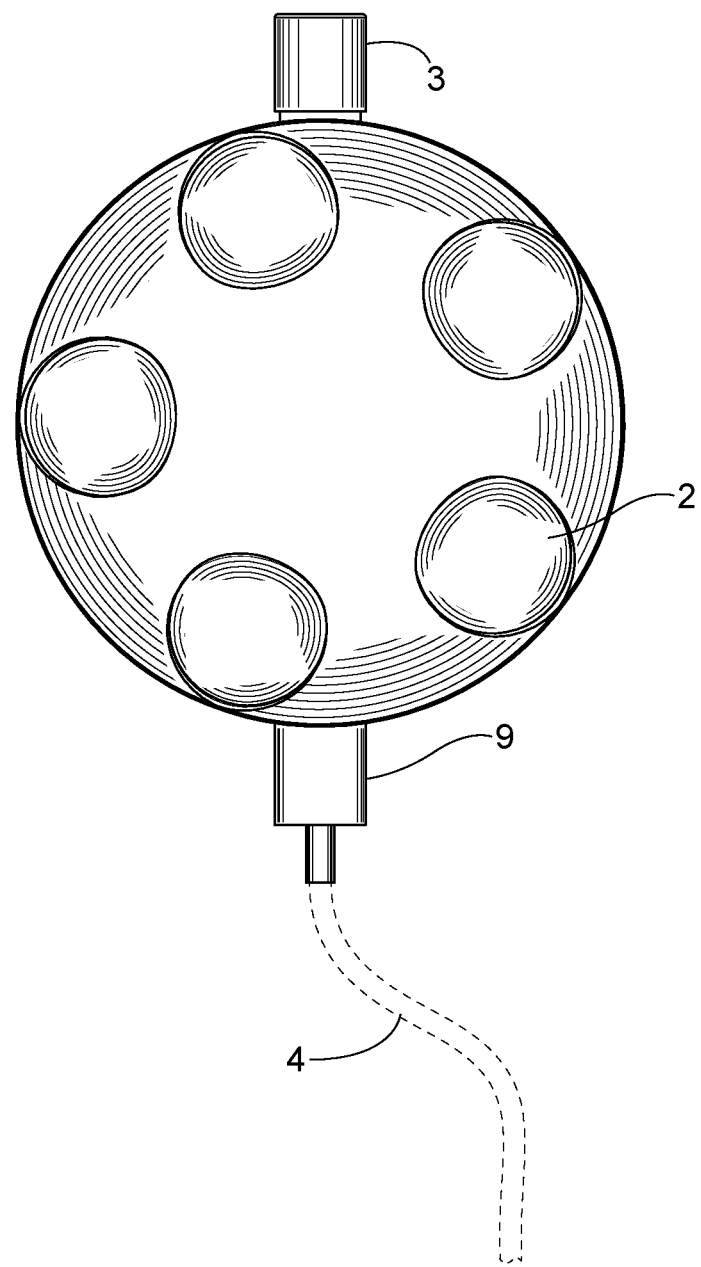

FIG. 6 depicts a top down view of the anchor 1. FIG. 7 depicts a bottom view of an embodiment of an anchor 1, having five feet.

Figure 18:
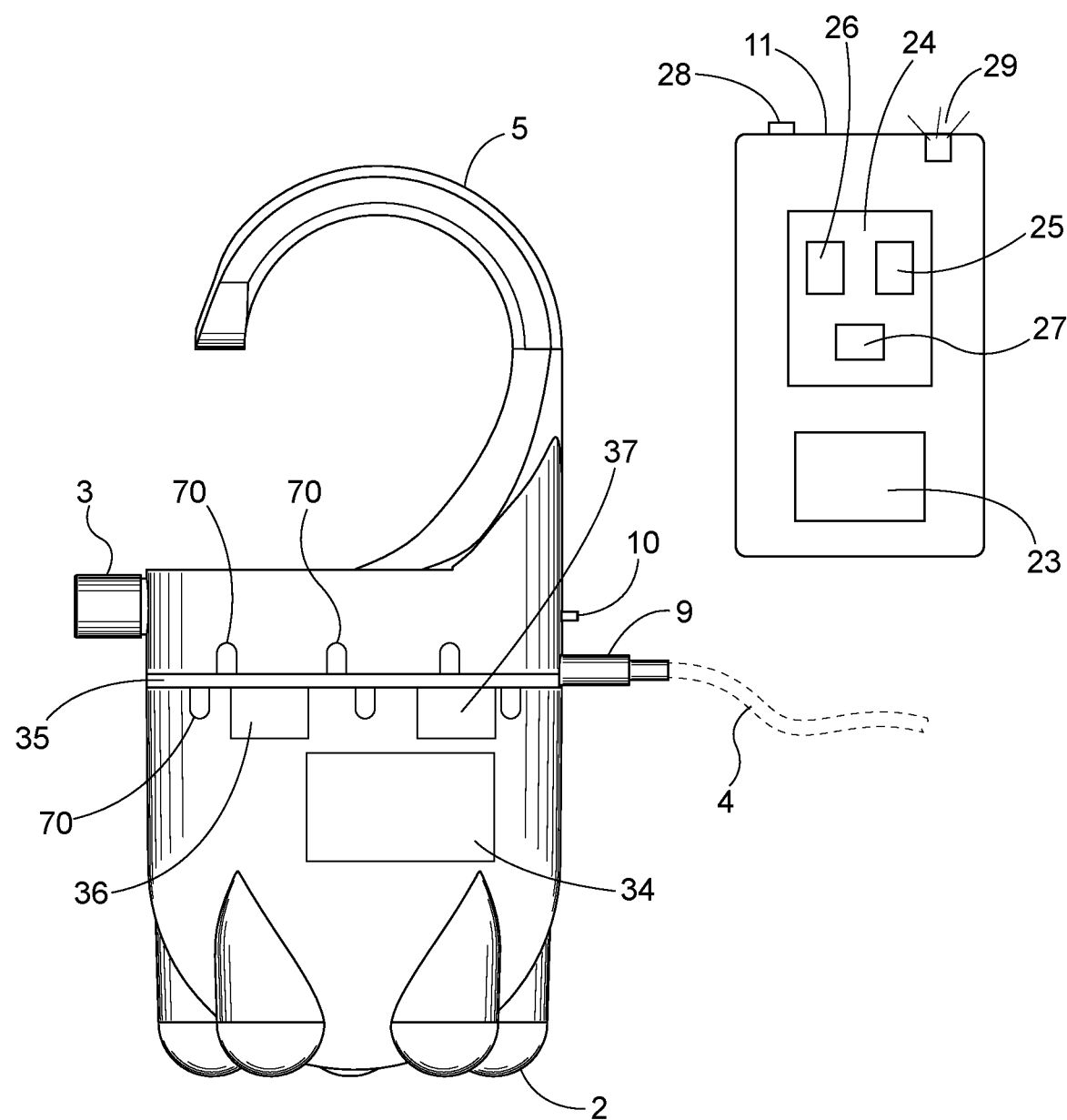
FIG. 18 depicts internal components of an anchor/light pod and of a tag.

Internal components of the anchor 1 and a tag 11 can be modified as necessary to implement the system and methods described herein. However, in an embodiment, FIG. 18 depicts an anchor 1, having a neck 5, a knob 3, a switch 10, a cord 4 with power adaptor 9. Internal components include a board with an attached processor, memory, and necessary components to electronically perform the tasks described herein. A sensor 36, and a wireless communication device 37 are provided. A battery 34 powers these components. Further light sources 70 are disposed inside of the base 7, for example at least one LED light.

FIG. 18 further details the internal components of a tag 11, including a battery 23, a board 24 comprising a necessary processor, memory, storage, and circuitry to perform the necessary tasks as described herein. A magnet 25 is provided in certain embodiments to allow for magnetic connection to a surface. A wireless communication component 26 provides for communication, e.g. between the tag 11 and the anchor 1. A switch 28, such as for turning the tag 11 from one action to another, e.g. on/off, or binary/non-binary control; a LED or light indicator 29. Additional memory or storage 27 is further provided to store data from the anchor.

Figure 13:
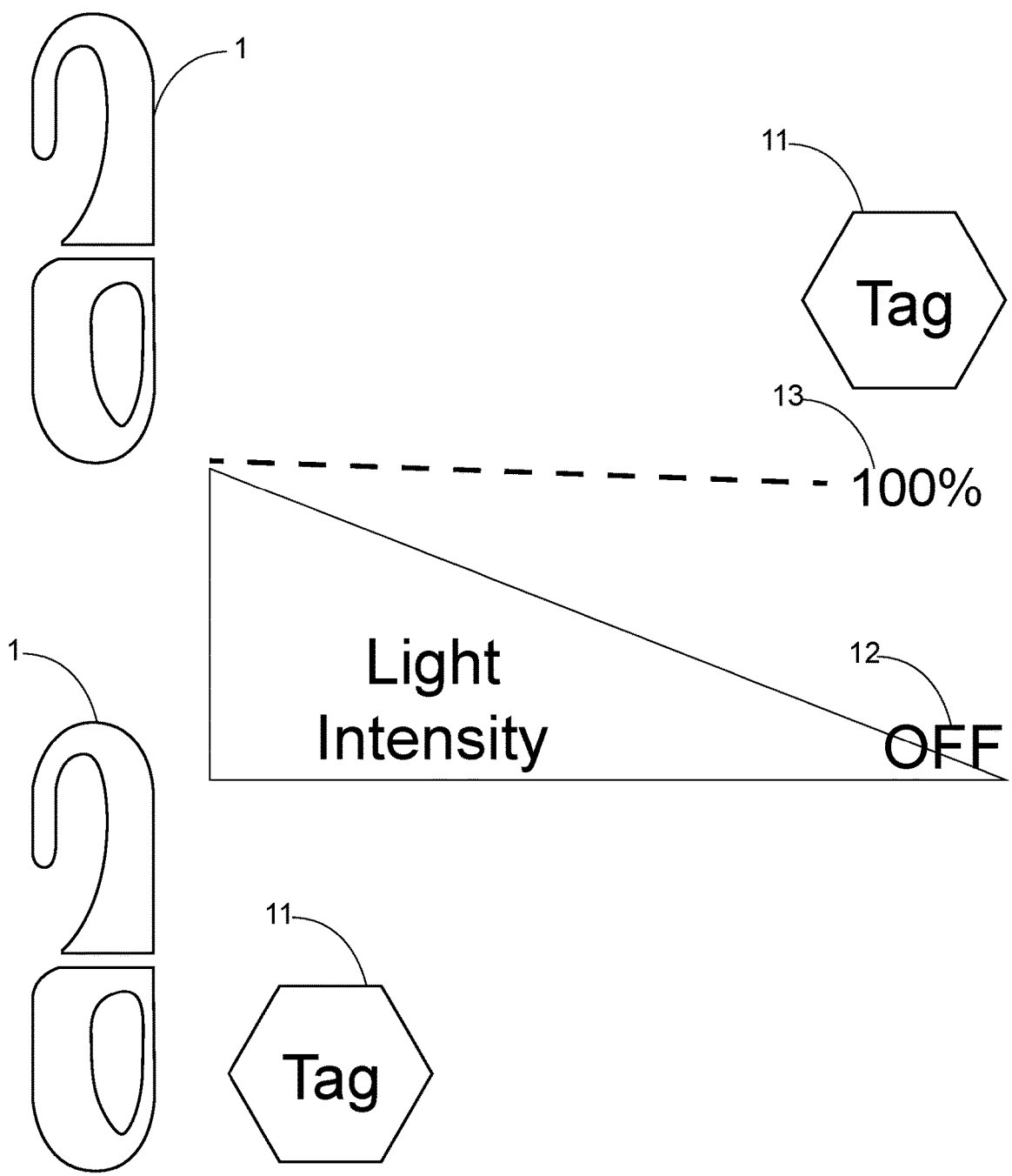

In the broadest sense, FIGS. 8 and 13 depict an embodiment of the lighting system, which comprises a tag 11 positioned with a nurse 20. The tag 11 provides an electronic communication 21 to the anchor 1, which turns on and turns off the light within the anchor. The activation of the light is controlled by the devices having a microcontroller that processes an input signal from a tag 1 to activate the circadian-friendly task light (light pod) of anchor 1.

For example, FIG. 13 depicts an embodiment of how the light intensity will operate, as a function of distance between the anchor 1 and the tag 11. When the anchor 1 is proximate to the tag 11, as shown at the bottom of FIG. 13, the light intensity is close to 100%. Conversely, when the anchor 1 is separated from the tag 1, the light intensity is reduced, until it reaches 0% or off. The light intensity scale off at 12 and 100% a 13 is shown between the two extreme examples.

So, as an example, the distance to engage the lighting anchor 1 may be a minimum of 8 feet, and thus, when a person, having a tag 11 enters to within 8 feet of the lighting anchor 1, the light will engage. As the person progresses closer to the anchor 1, the light intensity will increase. For example, 100% intensity may be reached when the distance between the anchor 1 and the tag 11 is a distance of between 0 and 1 feet. An example of the above situation might be a hospital room. A patient, having an IV line and an IV tree with a drip counter. A lighting anchor 1 is positioned to illuminate the drip counter. When a care provider enters the room and has a tag 11 on her person, the distance between the tag 11 and the anchor 1 is 8 feet, and the anchor illuminates slightly. As the care provider gets closer to the IV tree and the lighting anchor 1, the light increases in intensity. A quick check of the IV tree and the care provider can leave the room. As she walks away from the IV tree, the light decreases in intensity and finally is at zero output, as she leaves the room and the distance between the tag 11 and the anchor 1 is more than 8 feet and the light turns off, or to its otherwise predetermined setting.

The precise distances for zero intensity and 100% intensity can be modified based on the necessary provisions and uses. For example, a large room might need much greater distance before the anchor 1 illuminates. Similarly, it may not be possible to get more than within ten feet of an anchor, but 100% illumination may be wanted at that distance. Accordingly, the distance for zero and 100% intensity can range from a few inches, to many yards away.

In a patient care facility, for example: hospital, emergency room, home care, elder care, nursing home, surgical facility, long-term care, etc., these responsive LED devices can be utilized within a patient room where needed. For example, an anchor 20 can be attached to devices that are already present in a standard room—thereby maintaining normal architecture of patient rooms and reducing the cost for adoption.

For example, FIG. 8 depicts three situations of the anchor 1 being positioned on a rod 90, with the neck 5 hanging around the rod 90. The top 8 is depicted as opaque, with the sides of body 7 translucent to allow light to shine through the body sides 7. The neck opening 6 may be attached to a hook or nail or other fastener to maintain the anchor 1 in place. The middle image of FIG. 8 shows a nurse 20 with a tag 11 attached to a board. The tag 11 emits a signal 21 that is read by the anchor 1 and illuminates based upon proximity between the tag 11 and anchor 1. The feet 2 of the anchor 1 are positioned with three feet in the embodiment to allow secure positioning on a linear surface. The final image of FIG. 8 depicts a curved surface (dotted line) showing that the feet 2 can be positioned on a curved surface.

Figure 9:
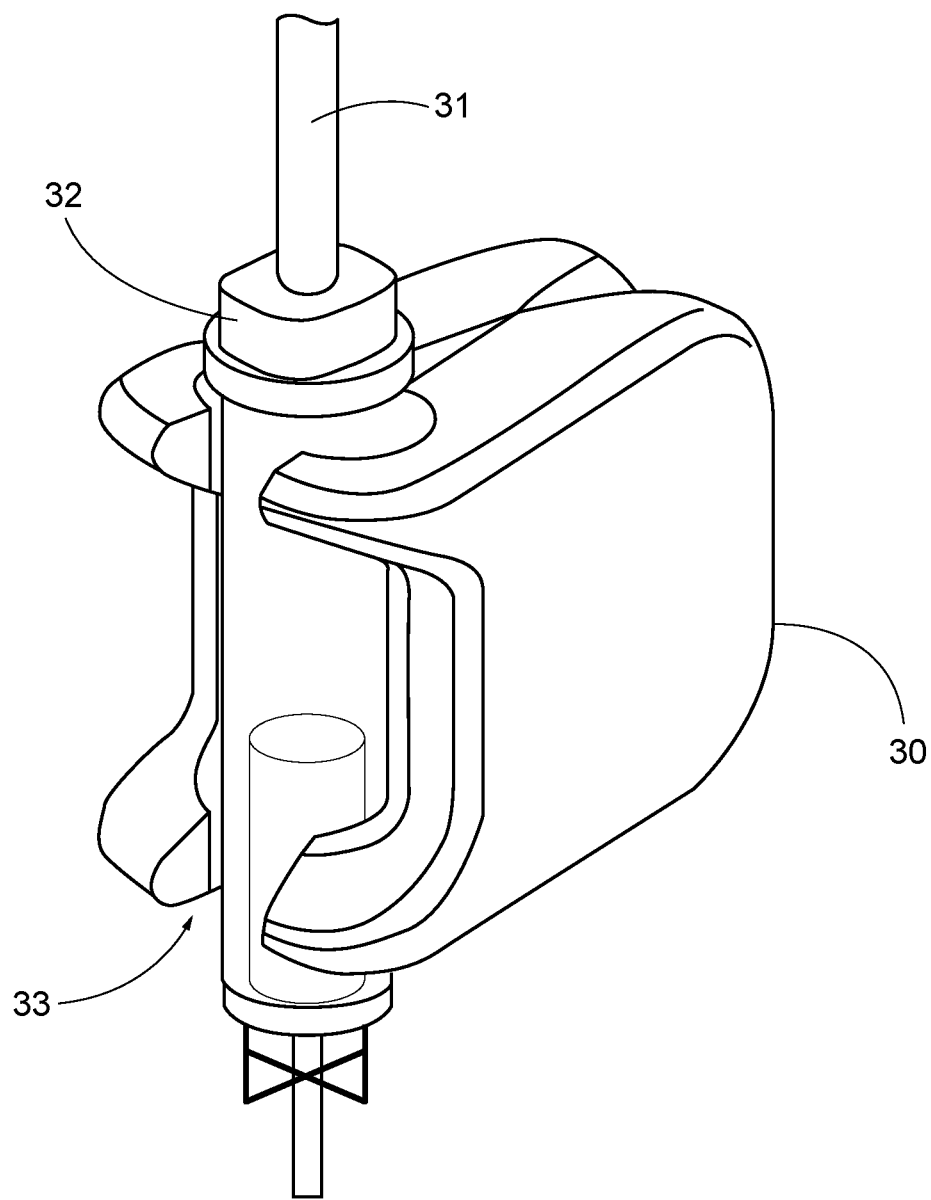

FIG. 9 depicts a further embodiment of a clip like anchor 30. The clip anchor comprises the same internal components as the prior anchor 1, but allows the clip anchor 30 to secure around some further device. FIG. 9 depicts a clip opening 33, which surrounds a drip chamber 32 having tubing 31 extending from the top and bottom of the drip chamber. A spring (not shown) can be utilized as known to a person of ordinary skill in the art to provide force to the clip to secure around an article. The internal faces of the clip can be translucent to allow for the internal light to pass through the material and illuminate the item that is within the clip.

For example, with clip anchor 30 positioned on an IV port connection, Foley Catheter, or other medical tube, tasks that would normally require overhead lighting can now be completed with localized, minimally-disruptive light. The IV-based device features diffusive as well as columnar light from the ends of the device—thereby turning any tubular structure into circadian-friendly flashlight that provides localized light where it is needed.

The battery life of the devices is specified to last for at least the full duration of an average patient stay (4.8 days according to the CDC). After discharge, the devices will be induction charged, after which they will be ready for immediate re-use.

The lighting constraints for an embodiment of the device mimizes light spectra in the 460-480 nanometer wavelength range, since these intensities are maximally disruptive to endogenous melatonin production. Preferably, the lights are low power consumption, such as light emitting diodes (LED), having light in the visible spectrum, but omitting or mimimizing light in the 460-480 nm wavelength range. Preferably the LEDs themselves are less than 2700 CCT with a minimum of 80 CRI. Mechanistically, they should all be capable of being activated through a proximity-sensing mechanism. Functionally, they must provide adequate, task-based illumination for the care provider. The appropriate bulb to emit visible light can further change based on the needs or application. Certain low power lights may be preferable in certain settings, but other settings may require a high intensity bulb. The appropriate bulb and light spectrum can be determined based on the needs of the device.

In a patient care setting, the devices preferably also satisfy the following criteria: their design allows for hands-free usage, is reusable, and easily sanitized for patient care. Furthermore, the battery life is operable for greater than or equal to 48 hours on a full charge. Preferably, the battery life is greater than 72 hours. The devices listed above could also be battery-powered with basic (rechargeable) AA/AAA batteries. It is expected that under ordinary use, the battery will last for between 5 and 30 days, and that an ordinary routine or replacement and charging will provide for consistent lighting. Furthermore, LED lights, as the battery decreases will provide lower output, but still illuminate, that providing a signal to charge or replace the device as necessary. Charging of internal batteries may be through an attached cord or wireless induction charging, as is known to a person of ordinary skill in the art.

In certain embodiments, regardless of care setting, the sensing component could also be adapted to use Bluetooth or iBeacon technology to allow for more 'smart' connectivity between many devices in a room. In certain embodiments, the sensing component tag 11 is an RFID like component that, upon proximity to an anchor 1 (lighting module), the sensing component/tag 11 engages to the lighting module 1 and engages or activates the light. However, any number of readers or communication mechanisms can be utilized to allow for consistent wireless communication based upon proximity between the devices.

Accordingly, the components are preferably described as a lighting system that responds to a user 21 (nurse, caregiver staff, parent etc.) proximity stimulus via wireless dongle or phone app tap. This system allows for automatic, proximity-based long-wavelength illumination of areas of interest in nighttime care.

Therefore, the system comprises at least one lighting module 1, at least one sensing component/tag 11, and at least one processor within the lighting module that computes and identifies the proper light to illuminate (see FIG. 18 for an embodiment depicting internal components). However, those of skill in the art will recognize the necessary hardware components to enable the wireless communication of the present system. The system then defines the necessary output and the appropriate lights are illuminated within the patient room.

In other embodiments, the components may be reversed, wherein a caregiver's module contains a processor holding the appropriate instructions, and wherein upon entry to a location with a light module, the module communicates with the processor to illuminate the proper lights. Furthermore, a room or space may contain a stand-alone processor that receives signals and communicates to illuminate the proper lighting modules.

This system, therefore, as depicted in FIG. 8 provides that when a nurse 21 enters a room to execute a task, a device/tag 11 on her person engages and/or communicates with a device 1in the patient room to provide the appropriate illumination based on a predetermined set of outputs. For example, during the day, certain programs may be used and at night different programs utilized. The goal of the outputs, specifically at night, is to illuminate only those spaces necessary for safety and for patient reconciliation. Once the task is performed and the caregiver leaves the room, the lights will slowly fade to off. This provides a gentle and non-stimulatory light into the patient room to prevent disruption of melatonin production and of sleep cycles.

Figure 10:
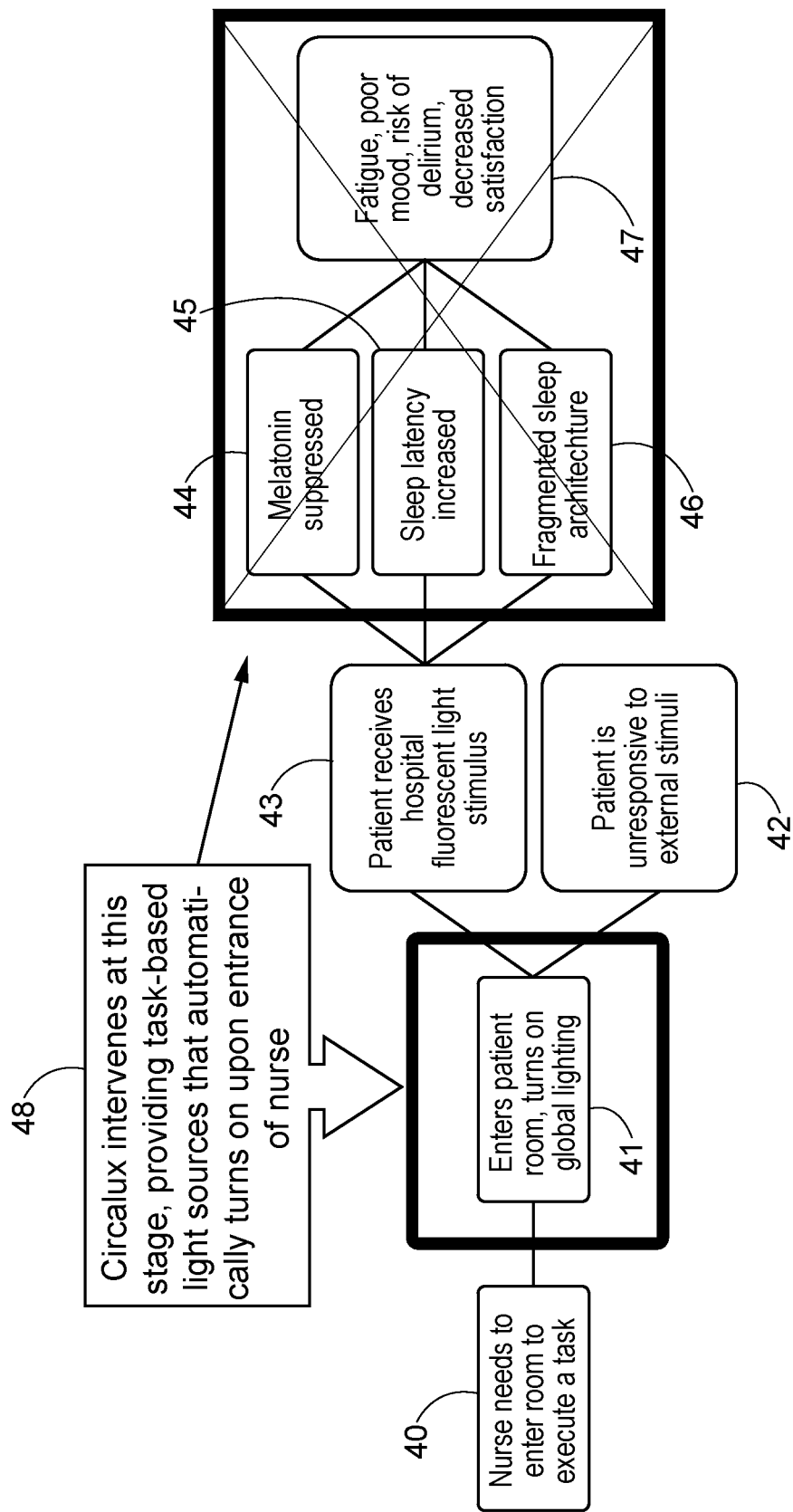

FIG. 10 depicts a typical patient care scenario, where a nurse enters a room to execute a task 40. By entering the room she turns on the global room lighting 41, patient is either unresponsive to external stimuli 42 or receives the fluorescent light stimuli 43. By receiving fluorescent light stimuli, melatonin is suppressed 44, sleep latency is increased 45 and fragmented sleep architecture 46 is generated. This leads to a result of increased fatigue, poor mood, risk of delirium, decreased satisfaction, as well as risks to healing and well-being 47. The invention seeks to intervene between steps 41 and 43, by eliminating the fluorescent light stimulus that is present in many care situations, both in the hospital, outpatient settings, and a home, wherein light impacts an individual resulting in the actions 44-47. By reducing the fluorescent light stimulus of 43, through task based lighting, these factors can be reduced or eliminated in such settings.

Figure 11:
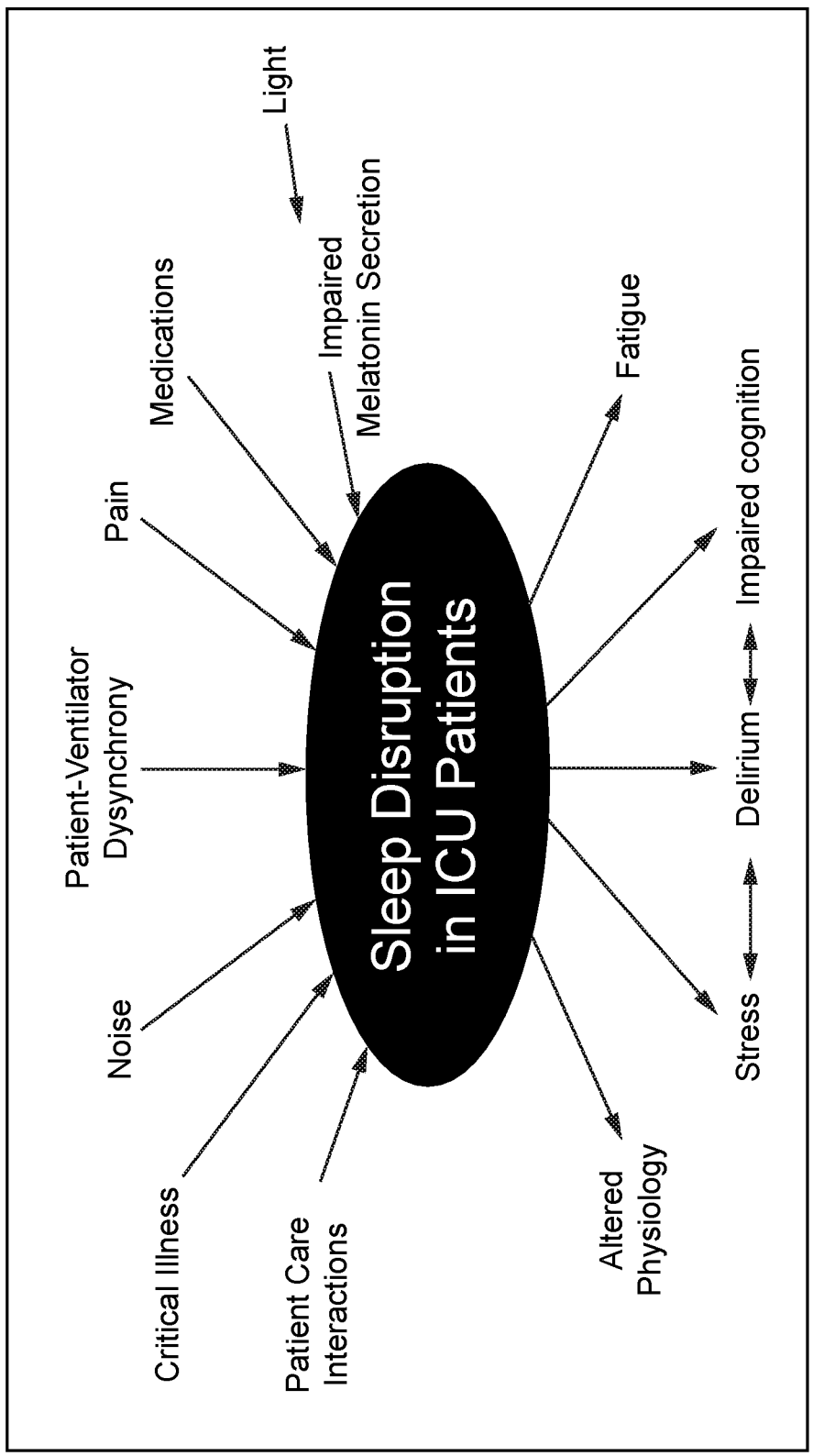

Indeed, FIG. 11 provides a visual of some of the expected and defined outcomes of sleep disruption in ICU patients. Light can directly impact sleep and cause significant disruption to a patient, thus reducing their outcomes.

Other embodiments are understood to flow naturally from this system. For example, hospital patients could also utilize this as a reliable and accessible nightlight. A patient themselves, might utilize a dongle or transponder that upon movement would illuminate the nightlight to light a path to the restroom. Other outputs might illuminate a reading light, etc. The system is customizable based on the needs of the user.

However, the benefit to the system is the simplicity of the hands free illumination system that provides minimize disruption to patient melatonin levels triggered by the use of overhead lighting in the patient room. Ultimately, this system provide hands-free, task-based lighting while minimizing staff physical contact with contaminated lighting fixtures in devices that will last the duration of an average hospital stay (approximately five days) on one charge.

The system therefore generates significant improvements in caregiver productivity and patient sleep quality can be achieved without changing the hospital infrastructure and do not require FDA approval, as the caregiver can automatically, without touching surfaces, perform tasks, and without waking the patient. Therefore, the system provides an alternative to expensive adaptive, circadian-friendly 'smart' lightbulbs and systems. Furthermore, in promoting better sleep, the system will reduce costly psychological conditions such as delirium.

Indeed, positive physiological effect of light richer in long-wavelength emissions will result in happier and more cooperative patients, improved healing and outcomes, shorter length of stay, improved patient satisfaction metrics, as well as better patient retention.

However, application of these devices is not limited to health-care settings, or, in particular to hospital settings. Accordingly, further variations may be more practical in other situations. Indeed, the present disclosure represents a method for a system of automatically activated, task-based lighting designed to be minimally disruptive to overnight melatonin production in humans. In the usage scenarios of hospital patients, circadian LED-equipped pods (other names "circalight(s)" or "anchor(s)") provide a low-cost, biologically-informed, environmentally-responsive lighting system that enables caregivers to do their jobs without disrupting patient sleep, hospital workflow, or patient room infrastructure. In the usage scenario of home consumers, circalights allow for night-time lighting for any task (i.e. going to bathroom, changing a diaper) that activates when the user approaches.

The selected LED technology in the circalight is commercially available, and it is a red-shifted light emission spectrum, which is less disruptive to melatonin production than current blue-rich hospital lighting. The LEDs are 80 CRI warm white light, allowing for accurate recognition of colors. The light output of the circalights is modulated by the distance of a sensor (also known as "tag") worn by the provider, from the circalight. The light intensity increases with smaller distance between these two components and decreases when the distance between tag and anchor increases (see FIG. 13). The circalights are small modular units that can be attached to railings and fixtures throughout the hospital room—thereby providing hands-free lighting to caregivers in the specific locations where they need light to perform care tasks.

In a preferred embodiment, a device comprises an anchor 1 and a tag 11, which communicate with one another to illuminate at least one anchor 1. FIG. 13 depicts a tag-anchor distance activation is in the form of UWB radio signals. UWB is designed to measure distance and location more accurately than narrowband systems like wi-fi or bluetooth. The radio signal used employs very short impulse transmissions, with sharp rises and drops, allowing for inherently easier measurement of signals' start and stops. This means that the distance between two UWB devices can be measured precisely by measuring the time that it takes for a radio wave to pass between the two devices. It delivers much more precise distance measurement than signal-strength estimation. The intensity, as described above in FIG. 13 is modified based on the distance between the tag and the anchor.

In consumer applications, distance-based interactions of a tag and an anchor can be applied to a wide variety of applications. If other wireless devices, such as smartphones, are equipped with UWB radio transmitters, they could become the tag (or anchor) and trigger events depending on the application. Therefore, a tag 11 may simply be a compatible smart device, such as a smart phone, tablet, or computing device that has such wireless connectivity. This would allow a user to simply use their existing technology devices to control the anchors 1.

The light anchor 1 can be manually switched on/off and have manual brightness adjustment via a physical knob 3. For example, a detail of the knob in FIGS. 1 and 2 depicts that the knob on the front of the device allows for switching into manual mode, where the device 1 is not responsive to the tag 11, and can be used as a standalone circadian-friendly pod. Furthermore, the knob 3 can control the intensity of the light, based on a function of distance.

Figure 17:
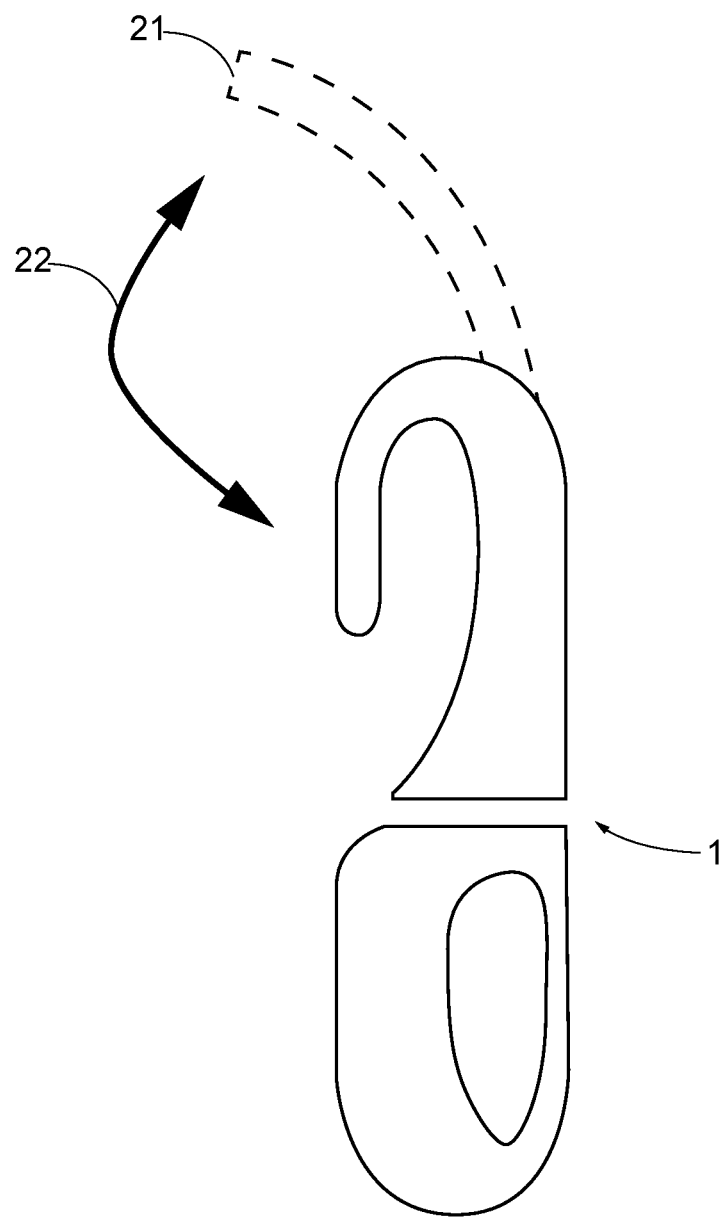
FIG. 17 depicts a variation of an anchor with a flexible neck.

With regard to the anchor, the top half of the device is designed to be a flexible hook 5, essentially a flexible plastic with a rigid bendable structure underneath, requiring a custom injection-molding approach. This will allow the device to be attached to a variety of structures (tubular, oval, rectangular, etc.) of various sizes in the environment, allowing for versatile location for the light. FIG. 17 depicts a variation where a flexible neck 21 can bend according to angle 22.

Preferably, the plastics used for each half of the device are selected for specific features. Both types of plastics must be resistant to frequent sterilization with chemical wipes (bleaches, alcohols, etc.) to prevent fading, color-changes, property changes when used in the medical industry, or in situations where they must be sterilized, however, the plastic for a non-hospital setting may not need to contain such plastics. For example an anchor in a bathroom of a consumer home, or a baby night light may not need to ever be sterilized. Accordingly, certain cost savings may be realized based on the needs of the consumer.

However, as shown in FIGS. 1-7, the base 7 of the anchor 1 is preferable translucent/clear to allow for accurate light diffusion. Lights may have a tint to the material, or be clear. Certain plastics that are appropriate are blow-moldable. The material may be rigid, or may contain some flexibility. Both the top 8 and bottom 7 portions of the plastic can be further coated with a lining, such as a film, rubber like material, or other clear or opaque material as necessary. For example a rubber-like material may cover the anchor and be easily removed. This would allow sanitation of the rubber-like cover material. Such material may further cover the neck 5.

The device contains a battery having sufficient capacity to ensure that the light can run for at least several days, without the need to re-charge the light. Typically, the light will only be on for a few minutes at a time. Thus, even with repeated cycles of a few minutes, the light battery will allow for several days of intermittent lighting. Testing the device yielded 4 hour continuous light time at maximal energy draw, which translates to several nights of use on a single charge if we assume multiple 5-minute light usages per night. However, battery capacity can be increased easily for a light anchor that needs additional duration.

Furthermore, a power cord 4 can be directed into the anchor 1, to reduce the need for the battery 34. In this manner, the anchor may run off of power from the cord 4. However, if there is interruption of the power supply, then the battery 34 can sustain the anchor 1 for several hours. This provides a robust system to allow for reliability in trying circumstances.

FIG. 12 details several possible input 50 and outputs 51 for the device. For example, when a tag 11 enters a room 50 the output is that the light turns on 53, with brightness a function of proximity. When a tag leaves the room 54, the output is that the light turns off or fades in intensity based on a function of proximity 55. Finally, manually turning on the light 56 can turn the light on or off 57.

In a preferred embodiment, the anchor 1 includes a sensor 36 (FIGS. 3 and 18). The sensor can function in conjunction with the wireless communication to allow certain features to activate or prevent activation based on the inputs from the sensor. For example a sensor may be a light sensor, a sound sensor, a rotation sensor, a vibration sensor, or combinations thereof. The sensor can function internally, or may use an external port 60 (FIG. 3) as necessary.

In a preferred embodiment, the anchor pod sensor 36 is an embedded light sensor, so that the device does not activate unless it is in a low-light (night) environment, therefore avoiding unnecessary battery use during daytime. Thus, for example proximity during daylight hours, with light in the room, would not illuminate the anchor. Similarly, if the anchor is positioned in a room with supplemental lighting that is illuminated, the anchor will not need to illuminate, if the room is already lit. The amount of light at the sensor can be modified to ensure that the anchor illuminates under conditions desired by the end user.

In a further embodiment the sensor 36 is an embedded sound sensor, which allows the anchor light to be activated in response to audio cues in addition to existing tag distance mode and manual knob mode. This mode can be turned on or off as needed. This is intended to activate the light with loud sound that lasts several seconds (such as a baby crying or an alarm), so that the light can actually function as a visual alarm in addition to audio events. For example, the sound may be set at a decibel level of more than 40 decibels for greater than 5 continuous seconds. Variations of the decibel level and the time can be modified be the user. The anchor 1 may comprise one or more sensors, and thus a light and a sound sensor may both be utilized together in a single anchor 1, as one non-limiting example. In a preferred embodiment, the anchor 1 will have both a sound and a light sensor. One to sense if it's dark, thereby allowing activation only when it is dark, and the other to activate if loud sounds (e.g. baby crying or alarm) is ongoing for >5 seconds and then→activate light. The anchor 1 can modify these parameters, e.g. the time until a light illuminates after the activation of a sound sensor, based on the needs and use of the device.

In particular, the tags 11 and anchors 1 will have mesh ability, in that a tag 11 and anchor 1 are not "locked" in together: any tag 11 can communicate with any anchor 1, and the algorithm for activation will be decided by the code on-board the anchor 1, so that any tag 11 that approaches will trigger that action. This setting can be controlled by the software. Thus, different tags 11 can also have different functions, as necessary by the particular application of the system. Thus multiple persons can service the same anchor 1 and each have the same or different light protocols as necessary for the application.

Figure 14:
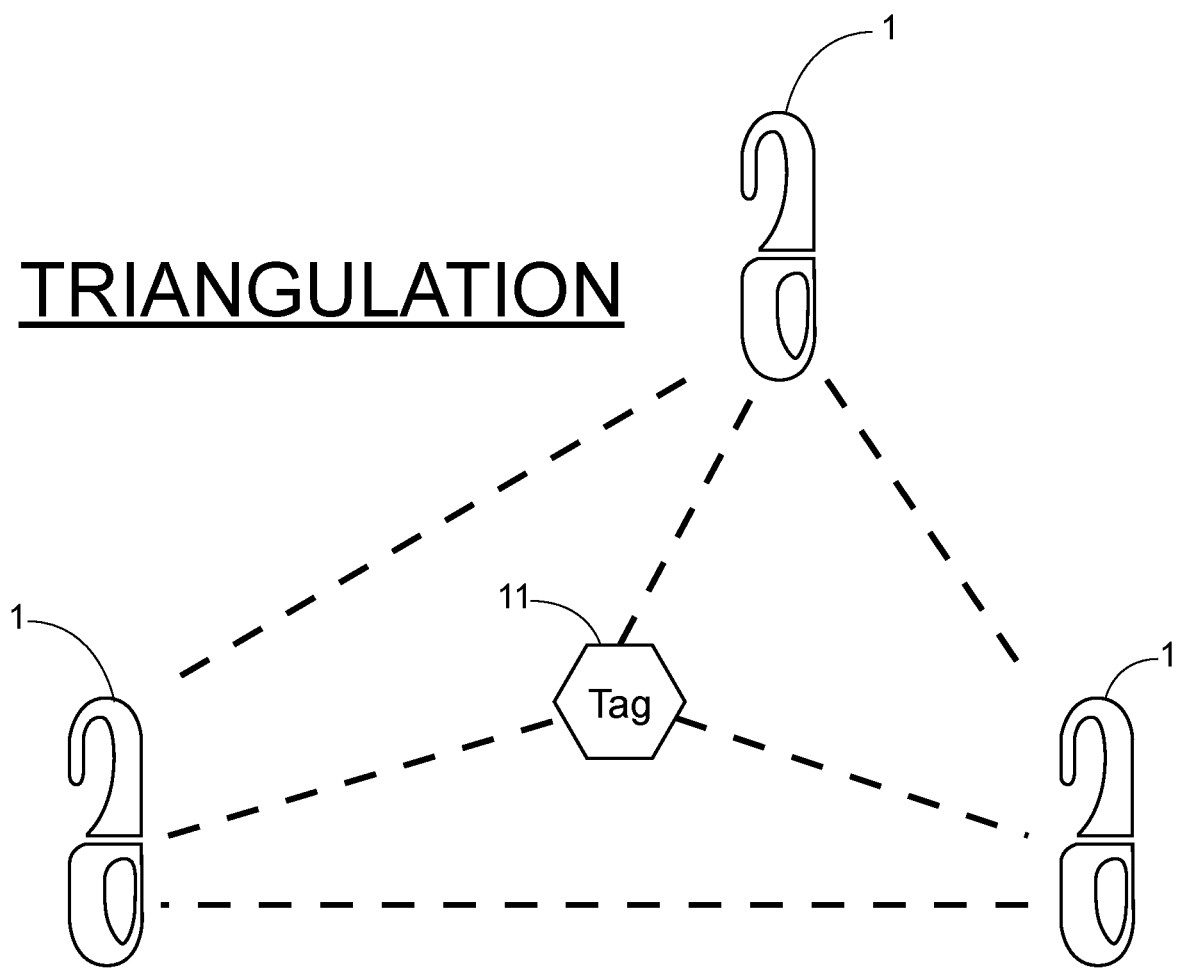

Accurate distance sensing can lend itself to practical applications where an anchor 1 can be embedded inside assets (automated manufacturing tools, warehouse operations, etc.) and a tag 11 can be used within the setup to improve precision or to simply track distance from asset. For example, the devices can perform triangulation as shown in FIG. 14. In other words by having at minimum three anchors 1, the distance-sensing capability already discussed can deduce the location of the tag 11 in 2D space (four anchors minimum for 3D space), relative to the anchors. By connecting one of the anchors to a computer, this information can be retrieved by the user, allowing real-time triangulation of a tag. The particular application of this feature allows for position location of a tag.

Indeed, FIG. 14 shows that triangulation involves at minimum three anchors 1 and one tag 11, wherein the onboard chips can calculate the exact position in 2D space of a tag based on its distance from the three anchors, resolution and range based on capability of UWB radio. Such uses can allow identification of a particular tag, which may be particularly helpful where the tag is connected to a person or thing, and the location of that tag 11 needs to be identified.

The tag-anchor algorithm can be applied to a more static application: the tag 11 can be equipped with a physical on-off switch 28 (FIG. 18), allowing the user to turn the anchor 1 on/off without needing to use distance as an activation parameter. This interface can use UWB, or it can be simplified to a 434 Mhz radio communication. Example: tags 11 with embedded magnet 25 (see FIG. 18) will allow placement (and easy removal) anywhere via a magnetic sticker or by placing on metal surfaces. Major advantage is that tag is a portable switch, can be placed anywhere within the user's space for customizable convenience, or can be carried around. Pressing the device once will turn the light pod(s) on/off. Press and hold to manually adjust the brightness of the light. The range of the device is consistent with the range of the communication signal. Thus a magnetic backing 101 can be affixed to where a consumer needs to have a light switch 100. The consumer then places a tag, as in FIG. 19 on a wall, the light switch tag 100 then secures to the magnetic backing 101 with magnetic forces 103. This allows for use of the switch or button 102 on the tag 100 to activate or deactivate a light anchor 1.

The tag-anchor communication can be Bluetooth, allowing for more expansive tag options. In other words, the tag can be any Bluetooth-enabled device on the market. The tag-anchor communication could also be adapted to use iBeacon technology, Zigbee mesh, Z-wave, thread network protocol to allow for different 'smart' connectivity between the anchor and its environment.

The code onboard the anchor does not need to solely define activation of LEDs, if the anchor is an embedded electronic, the distance-based activation via a tag can trigger whatever the user intends that electronic to do. For example, if anchor is a wall electric plug, it can activate devices inserted into it based upon distance from tag. Other actions: turning on radio when entering room; security camera turning on.

Tags and anchors can be used, with triangulation capabilities and accurate distance sensing, for digital hotspotting and geospacing. This can allow for a variety of applications: from resource tracking to epidemiological research.

Further applications of the system:

The lighting system provides localized, task-based lighting for staff to not disrupt sleep in almost any hospital inpatient setting—including oncology, pediatric, NICU, and surgical step-down units. The responsive algorithm can also be applied to care of other patient populations such as child nurseries and geriatric populations in LTCF.

Embodiments could also be equipped with inter-device 'Internet-of-Things' connectivity to accommodate specific in-patient care scenarios. For instance, when a crash cart enters a patient room for an emergency, the proximity-sensing mechanism is overridden and will trigger the normal overhead lighting fixtures to turn on. Additionally, the patient will have the opportunity to turn the anchor lights on themselves, whether they need light to see something at night or just for comfort. This adaptability further tailors the solution to meet the needs of hospital care.

The automated task-based lighting system can be tailored to the surgical theater, wherein an overhead device made up of LED arrays would track surgeon hand gestures and location in the frame, to provide triangulated light to the visual field, thereby reducing the need for touching and adjusting lamps and eliminating shadows.

In long-term care facilities (LTCF), the device can be attuned to respond to pressure stimuli to replace the disruption of a normal bed alarm system: when a resident tries to get out of bed at night, their position will be communicated to the responsive lighting device via a pressure sensing mat on the bed. When null pressure is sensed, the device will illuminate the area around the bed for as long as the distributed pressure of the patient's weight is not sensed by the mat. This mechanism provide light for the patient and signals to the staff that the patient is out of bed—thereby preventing or reducing fall risks. Beyond triggering the local lighting device, the information that the patient is getting out of bed can be wirelessly communicated to the staff.

In certain embodiments to combat Sundowner's Syndrome in LTCF, an adjustable hospital curtain outfitted with LED mesh will be positioned around the patient's bed in dual-occupancy rooms. Prior to their normal bedtime, a care provider will draw the curtain around the patient, who will be exposed to indirect, high-intensity light for one to two hours, which has been scientifically shown to improve the quality of sleep in dementia patients. At night, the curtain will become responsive to a proximity sensing dongle worn by the care provider, who will be able to initiate red-shifted lighting to complete nighttime tasks. The provider engages the curtain by touching its surface and swiping upwards in a fashion similar to a dimmer switch. In this way, the curtain serves a dual purpose in providing evidence-based means to better sleep in patients with Sundowner's syndrome while equipping staff with minimally-disruptive light.

In the home consumer market, the system can be applied to light devices that will make infant rooms during the evening and night-time more sleep-friendly and easy for caretakers to have automated light when they need it (check in, diaper change, feeding, etc.). In a society where light pollution and usage is becoming a bigger factor in sleep, it will be important to ensure that growing children are poised to have the best rest they can get.

A particular benefit of the systems and methods described herein is the use of proximity sensor mechanisms in conjunction with the red-shifted light provides for appropriate wavelength light to reduce disruption of sleep cycles, while at the same time provide the appropriate amount of light to perform a task. As the sensor moves closer to a lighting module, the intensity of the light is increased. Thus, wherein a user needs to get close to a space, the intensity will increase to provide sufficient light to perform that task. One the user decreases the distance between the light module and the sensor, the light intensity decreases.

In, for example, an infant bedroom, this would allow someone to enter the room, provide a small amount of light to check on the infant, and retain a low level of light, if distance from the crib or bed is maintained. If a parent or caregiver needs to move closer to the child or light source, then the light will increase to allow for appropriate illumination of the area.

In certain embodiments, the light can be programmed to define the max or min intensity, as well as to provide a timer to maintain the light at a certain intensity for a duration despite the removal of the sensor.

The method proposed herein represents a system of automatically activated, task-based, circadian-friendly lighting. Examples of these applications include circadian-friendly light pods with a physical design allowing for versatile placement. The flexible hooked top allows for easy hanging and placement while the base enables stability.

An advantage of UWB in certain embodiments is that the use of existing technologies, such as Bluetooth, only detect proximity by comparing weak and strong signals, which informs the device that the object being tracked is in range. However this does not allow for the precise measurement distance or tracking location. Estimating distance by extrapolating from signal strength suffers from low resolution and other confounders that affect signal strength: this is a challenge in bluetooth and wi-fi systems. Wi-fi, bluetooth, and other narrowband radio systems only have accuracy of several meters. Yet, in many applications, such precise distance control is not necessary and thus these wireless tools are sufficient for those applications.

UWB signals maintain their integrity and structure even in the presence of noise and multi-path effects. Due to the shortness of the radio pulse, multi-path effects will typically not overlap with the true signal, thus not damaging the integrity and strength of the true signal. This is why UWB naturally allows for not only distance measurement, but also location tracking via triangulation.

In hospital settings, these responsive LED devices will be attached to devices that are already present in a standard room—thereby maintaining normal architecture of patient rooms and reducing the cost for adoption. We hope to achieve minimal effect on existing infrastructure: no need to plug bulbs into sockets or run wires. The lights will have flexible hook-like top half which can be molded and wrapped around objects of different sizes and shapes (cylindrical, rectangular, triangular, etc.); what would normally require overhead lighting can now be completed with localized, minimally-disruptive light.

The battery life of the devices is designed to last, a bare minimum, for the full duration of an average patient stay (4.8 days according to the CDC) in average use scenarios. This is based upon an aggressive estimate of 8-12 5-minute room entries with the tag. Between uses, devices will be recharged (both the light and tags) and wiped down with hospital disinfectant wipes (alcohol and/or bleach-based). In turn, the materials used for the bottom of the device will be translucent plastic compatible with hospital disinfection and resistant to physical changes (especially color and light transmission). After discharge, the devices will be re-charged, after which they will be ready for immediate re-use.

Additional implementation of this technology in other health-care settings, includes: nursing care, assisted living facilities, and in the home. As a circadian-friendly nightlight (with some extra features), these devices are practical anywhere light is needed at night. Much like in the hospital environment, the lighting system described herein are well-adapted to other care spaces. A young mother who has to wake up frequently to change a diaper, feed, or check on a child would benefit greatly. A baby's crying can activate the device via voice activation or the mother can enter the room carrying the transmitter and activate the light while caring for her child's needs. When she is finished, the light will turn off automatically when she leaves the activation radius.

An older man suffering from BPH will also be waking multiple times in a night to use the restroom. Strategically positioned circalights on his night stand and in the bathroom will allow him to take care of his needs with adequate lighting with minimal disruption to his melatonin production. Similar case scenario could be considered with new parents, and needing light to change a diaper or nurse several times throughout a night.

Nurses in elderly homes will also be able to take care of their patients nightly needs without disrupting their sleep. They can perform simple tasks such as IV bag changing, and vitals check with adequate light.

However, the home and patient care is not the only possible use and the lighting system can be implemented in any location wherein light, whether general or focused is necessary.

Examples of the system in use:

An anchor, as depicted in FIG. 18 comprises therein blue-deplete warm white LEDs 70, a UWB radio 37, a light sensor 36, a sound sensor 36, a battery 34. The components contain an electromagnetic field that surrounds the anchor for detecting and receiving a signal from a tag 11. The tag 11 is a key fob equipped with UWB radio 26 and battery 23.

Entry into a room, e.g. as in FIGS. 12 and 13 engages the field. The point of activation is 8 feet between tag and anchor. When the tag is more than 8 feet away the anchor is inactive and will remain so unless the tag is brought closer or manual or sound modes are activated.

Entry further into the same room, E.g. FIGS. 12 and 13, engages the light further. When the tag is located less than 1 foot away, the anchor light operates at maximum brightness, useful for task-based lighting.

Example 2

Three lights on a system—placement of component within system, can identify the relative location of a person holding component as depicted in FIG. 14 depicting triangulation.

Example, at a living center, there are positioned three anchors 1 within a certain area. John Smith, a member of the living center, did not appear at meeting. John Smith is wearing a tag 11. We can triangulate the position of the tag 11 normally with John Smith to identify position. This can allow quick and easy identification of the location of a person without more intrusive auditory alarms or requests to locate the person.

The information on location can be relayed to a computer with UWB radio attachment, locating John Smith in a room engaging with other individuals, and thus no further engagement or interaction is needed. Relative distances between the tag 11 and each anchor 1 can be calculated via the software and processor in the devices, and relative distances calculated to identify the location of the tag 11 between the three or more anchors 1. Accordingly, in the example, John Smith can be found through triangulation of his tag 11 between a grouping of anchors 1, and provided with information, medication, or some other action, as necessary.

Example 3

Multiple tags with a physical on/off toggle can relay an electromagnetic signal to anchors. This creates a system of light switches that can be moved and placed anywhere in an environment. This system is ideal for those uninterested in carrying a transmitter as it is hands-free and does not require a separate tag for triggering purposes.

Figure 19:
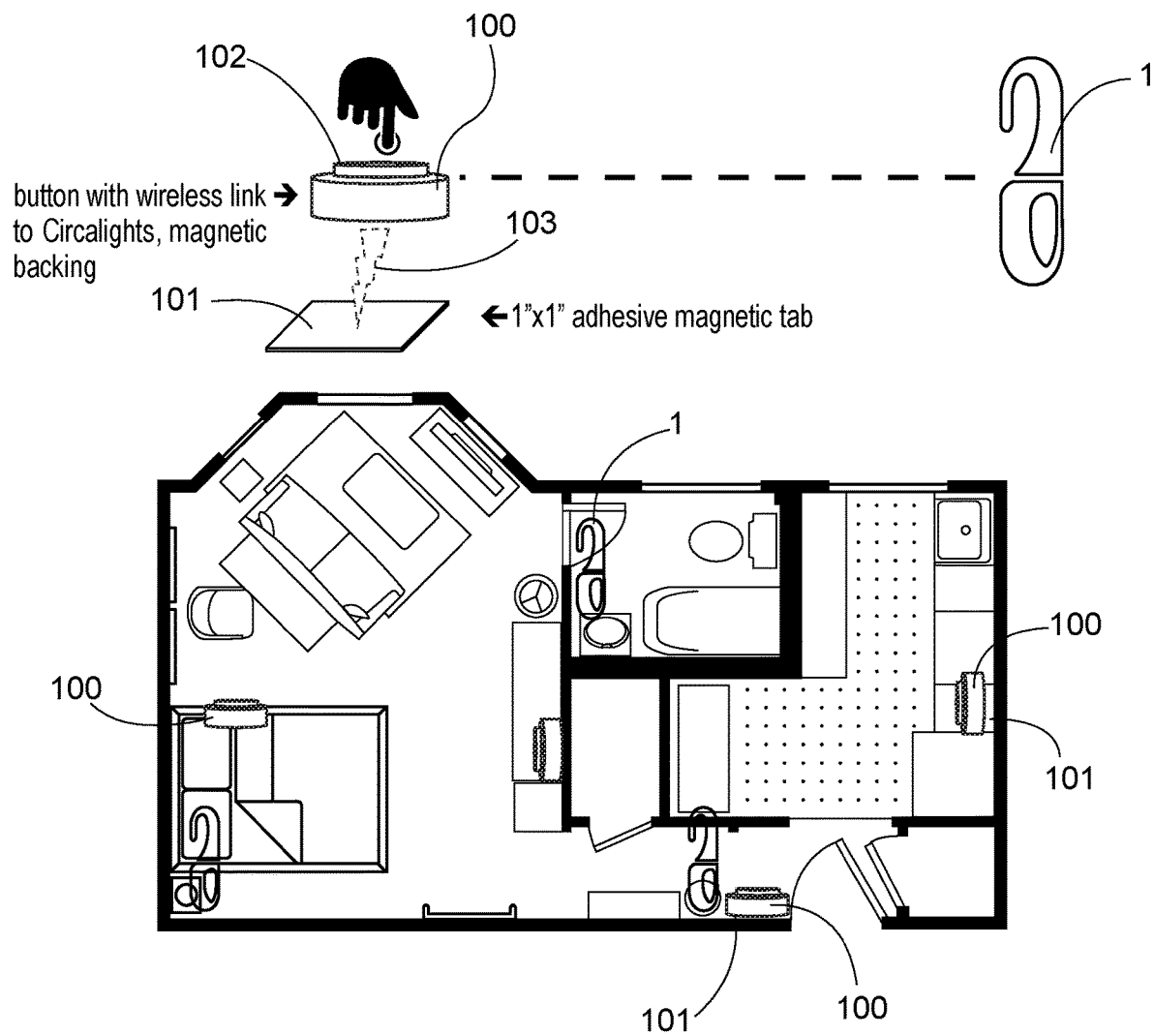
FIG. 19 depicts an embodiment using magnetic backing to activate an anchor with one touch.

Example, in the home, FIG. 19, Mary has difficulty ambulating and has poor eyesight. She has placed magnetic stickers 101 and magnetically attached tags 100 on her bedside table as well as in other easy-to-reach locations in her house. She wakes up in the middle of the night to go to the bathroom, touches the tag switch 102, and the anchors 1 (i.e. circalights) instantly turn on at the brightness level she already set, wherever they are in the house (i.e. bathroom in this scenario). This provides for a direct binary control of an anchor 1 based on the necessary settings for the user, and allows for easy location and placement of tools to assist the individual with safely lighting the space for the user.

Example 4

In the surgical field, lighting needs to be constantly adjusted by an operator manually to obtain the best view of the field.

Example, precise distance sensing with UWB tags and anchors could allow for triangulation of the surgeon's hands if he is wearing a UWB tag and if there are anchors on edges of operating room bed; this can allow automation of light fixture to automatically light an area near the hand/tag.

Example 5

Figure 15:
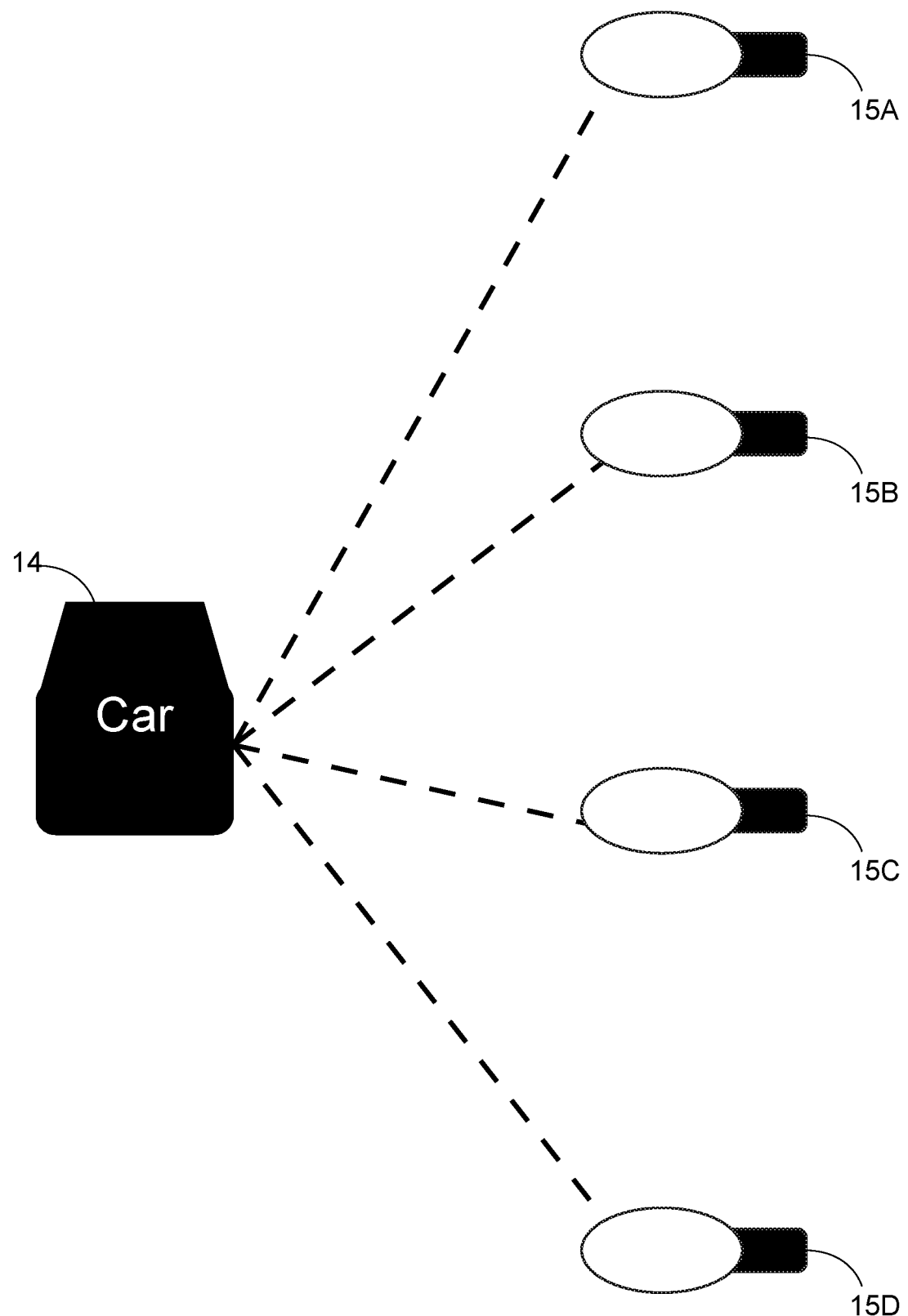

Vehicles equipped with UWB tags can communicate with an anchor-equipped environment. FIG. 15 depicts a UWB equipped car 14 and infrastructure (street lights) 15A, 15B, 15C, and 15D, allowing for localized usage of electricity in low traffic roadways.

Example, if vehicles 14 were equipped with tags and street lights 15A-15D were anchors (with carefully mapped distance algorithms), lights could turn on and turn off as vehicles need (saving significant amounts of energy in low-traffic areas). Along a similar line, UWB could allow for inter-vehicular distance sensing for more accurate mapping of obstacles in space in automated vehicle applications.

Example 6

If an anchor functions as an electrical on/off switch, multiple anchors can bridge between existing electronics/lights.

Example, John installs the UWB anchor on the electrical outlet for multiple devices around his house. John, having a tag on his person, approaches his home in his car. The garage door, gated by UWB anchor automatically opens when he is 20 feet away and closes when he is 1 foot inside. The lights on to which he installed the anchor gates have already been triggered by his arrival as well. Accordingly, the anchor can function as an electronic relay to activate some switch upon sufficient proximity between the anchor and tag.

The UWB anchor can communicate other information as well, such as linking with smart devices to further allow customization of device output. Example, retrofitting other lighting devices with UWB anchor also makes them more circadian-friendly by changing the LED output at different times of day/night.

Example 7

UWB systems can allow for more data transmission between tag and anchor, beyond distance sensing: conveying vital signs and other information pertinent to care.

Example, Dr. Brown has his smartphone out, checking patient information. UWB tags in patient rooms are embedded or connected to various devices (vitals monitors, fluid drips, lab result readers, etc.). Information is relayed into the hospital electronic health record via UWB nodes that are connected to the local hospital network. This information is relayed to Dr. Brown's phone via existing hospital wireless internet.

Example 8

Figure 16:
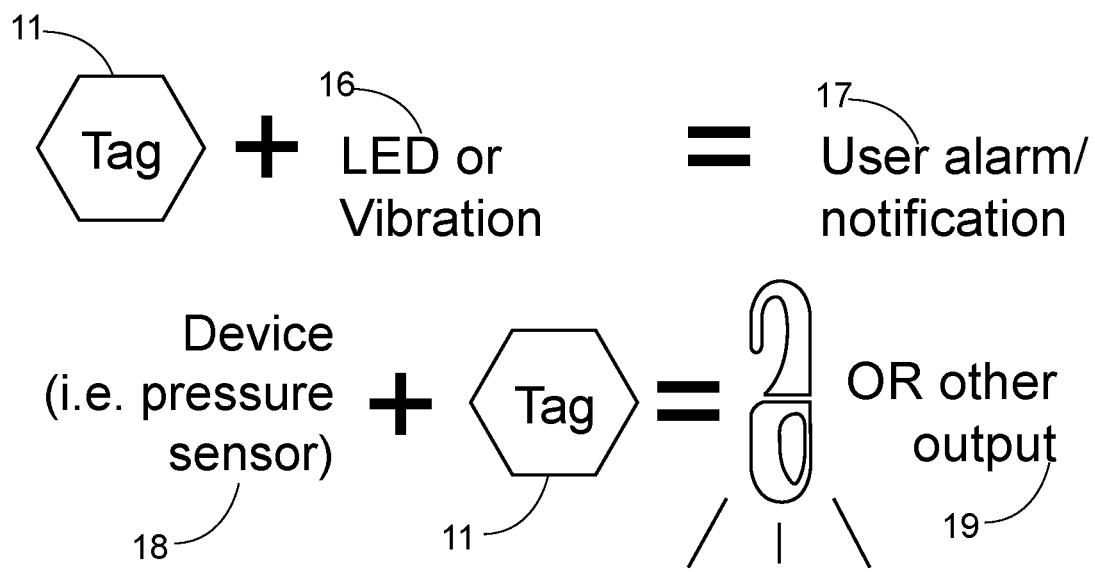

Keeping in mind that tags are simply UWB transmission beacons, they can have various embodiments. For example, existing physical sensors can be linked to UWB tags, thereby having UWB connectivity and ability to interface with other devices. In this example, we have two different tags: one that is either connected to a mattress pressure sensor, and one that is a wearable fob, but possessing physical output (i.e. vibration or a flashing LED). For example FIG. 16 depicts that a tag 11 can have embedded vibration or small led lights to alert the tag-holder, as UWB transmission is two-way (i.e. the tag can receive input from an anchor and start vibrating). When embedded in a pressure sensor, it can convey information to the anchor based on the output of the pressure sensor. The firmware on the hardware will dictate the functionality.

In long-term care facilities (LTCF), the tag can be in various embodiments: as a fob equipped with vibration (or light) that caregivers wear, or as a pressure sensor in patient beds. The latter tag can respond to pressure stimuli to replace the sound disruption of a normal bed alarm system: when a resident tries to get out of bed at night, their position will be communicated to the anchor circalights via the UWB tag-connected pressure sensing mat on the bed. When null pressure is sensed, the circadian-friendly lighting will illuminate the area around the bed for as long as the mat does not sense the distributed pressure of the patient's weight. This setup provides light for the patient and the mattress tag also triggers a signal to the tag-wearing staff that the patient is out of bed by vibrating their wearable tags. Beyond triggering the local lighting device, the information that the patient is getting out of bed can be wirelessly communicated to the staff without sounding a disruptive alarm.

Example 9

The anchor may also take a different physical form to provide circadian-friendly light. Many hospital and facilities have room-sharing for patients and residents, and these patients are separated by a simple fabric curtain. In dual-occupancy rooms, an embodiment of the anchor is as an LED mesh that can be hung on to the curtains (or integrated into the fabric itself), using the existing curtain hanging infrastructure. Opening the curtain will activate it so that it is responsive to UWB tags that providers are wearing, so that any provider walking in at night-time with a UWB tag will trigger the soft adjustable circadian-friendly light emitted by the mesh. The mesh characteristics can be adjusted, where the user only wants light from the bottom 2 feet of the curtain, only that segment will illuminate.

In preferred embodiments, to minimize effect of light intensity on melatonin eye receptors, we strive to keep max light intensity less than or equal to 40 lux. In preferred embodiments, the lighting constraints for light anchor 1 devices are as follows: They preferably minimize light spectra in the 460-480 nanometer wavelength range, since these intensities are maximally disruptive to endogenous melatonin production for health-care applications. The LEDs themselves must be less or equal to 2200K CCT with a minimum of 80 CRI. Mechanistically, they feature a tag and anchor format of activation: anchors 1 communicate with tags 11 through UWB and distance-sensing algorithm, but other iterations of tag and anchor setup may communicate with other means-such as radio frequencies, other wireless frequencies, optical mechanisms such as infrared. Functionally, they must provide adequate, task-based illumination for the care provider, with a tunable light intensity. There should also be a manual toggle on the light for activation and dimming.

The devices must also satisfy the following criteria: Their design must allow for hands-free usage, must be reusable, and easily sanitized for patient care. Furthermore, the battery life must sustain maximal energy setting (e.g. distance-sensing while at maximum brightness) for no less than 4 hours, preferably 6 or 8 hours, when wireless, with indefinite lifetime when having a direct plug application.

UWB tag-anchor communication can also allow for more accurate mapping of resources in space via distance-sensing compared to existing wireless communications.

UWB tag-anchor distance sensing can allow for precise interactions between users and physical devices, so that devices in space will activate based on the movement and distance to users equipped with a tag. UWB in portable electronic devices will allow for personal electronic devices to become the tag, performing the same role for the anchor.

However, other embodiments may use other wireless communication strategies, wherein the light is activated in an on/off binary choice. At a certain proximity, e.g. 8 feet, the light is on, at the maximum point it will illuminate based on a current setting. When the tag 11 and anchor 1 are separated by more than 8 feet, the anchor light 1 is off. This provides a simple on/off binary option for the light.

Other variations and embodiments are envisioned wherein the intensity and duration are modifiable by the end user to the particular situation as would be understood by one of ordinary skill in the art.

REFERENCES

Bedrosian, T. A., and R. J. Nelson. "Influence of the modern light environment on mood." Molecular psychiatry 18.7 (2013): 751-757.

Bourne, Richard S., and Gary H. Mills. "Melatonin: possible implications for the postoperative and critically ill patient." Intensive care medicine 32.3 (2006): 371-379.

Chellappa, Sarah L., et al. "Acute exposure to evening blue-enriched light impacts on human sleep." Journal of sleep research 22.5 (2013): 573-580.

Ely E W, Shintani A, Truman B, et al. Delirium as a predictor of mortality in mechanically ventilated patients in the intensive care unit. JAMA. 2004; 291(14):1753-1762.

Friese, R. S., Diaz-Arrastia, R., McBride, D., Frankel, H., & Gentilello, L. M. (2007). Quantity and quality of sleep in the surgical intensive care unit: are our patients sleeping?. Journal of Trauma and Acute Care Surgery, 63(6), 1210-1214.

Girard T D, Jackson J C, Pandharipande P P, et al. Delirium as a predictor of long-term cognitive impairment in survivors of critical illness. Crit Care Med. 2010; 38(7): 1513-20.

Kamdar, B B. Knauret, M., Jones, S.; Parsons, E.; Parathasarthy, S. (2016). Perceptions and Practices Regarding Sleep in the ICU: A Survey of 1,223 Critical Care Providers. Annals of the American Thoracic Society.

Koninklijke Philips Electronics N.V. HealWell—A New Lighting Solution for Patient Rooms. N.p.: Koninklijke Philips Electronics N.V, 2011. HealWell-Philips Lighting. Koninklijke Philips Electronics N.V, December 2011. Web. 29 Apr. 2016.

Leslie D L, Inouye S K. The Importance of Delirium: Economic and Societal Costs. Journal of the American Geriatrics Society. 2011; 59(Suppl 2):S241-S243. doi: 10.1111/j.1532-5415.2011.03671.x.

Milbrandt E B, Deppen S, Harrison P L, et al. Costs associated with delirium in mechanically ventilated patients. Crit Care Med. 2004; 32(4):955-962.

Rubin, F. H., Neal, K., Fenlon, K., Hassan, S., & Inouye, S. K. (2011). Sustainability and scalability of the hospital elder life program at a community hospital. Journal of the American Geriatrics Society, 59(2), 359-365.

Satlin, A., Volicer, L., Ross, V., Herz, L., & Campbell, S. (1992). Bright light treatment of behavioral and sleep disturbances. American Journal of Psychiatry, 149(8), 1028.

Thomason J W, Shintani A, Peterson J F, Pun B T, Jackson J C, Ely E W. Intensive care unit delirium is an independent predictor of longer hospital stay: a prospective analysis of 261 nonventilated patients. Crit Care. 2005;9 (4):R375-R381.

Van Someren, E. J., Kessler, A., Mirmiran, M., & Swaab, D. F. (1997). Indirect bright light improves circadian rest-activity rhythm disturbances in demented patients. Biological psychiatry, 41(9), 955-963.

Weinhouse G L, Schwab R J, Watson P L, et al. Bench-to-bedside review: delirium in ICU patients—importance of sleep deprivation. Crit Care. 2009; 13(6):234.

What is claimed is:

1. A system to provide circadian-friendly lighting for nighttime hospital care comprising:
   a lighting module anchor including:
   a body that encloses a proximity sensor system, a processor, a light emitter configured to emit red-shifted light spectra;
   the body including a translucent portion that at least partially encloses the light emitter;
   the body further including a plurality of hanger portions, the hanger portions including a curved neck, and a portal, wherein each hanger portion is formed to suspend the body from a different type of mounting point;
   the body further including a set of one or more feet that are formed to support the body on a surface;
   wherein the lighting module anchor is configured such that light output of the light emitter is modulated based on proximity of a tag, to the lighting module anchor, the tag being coupled to a caregiver, with light intensity of the emitted light increasing with closer proximity between the tag and the proximity sensor system, and decreasing with increased distance therebetween, with the tag being in communication with the proximity sensor system, such that the lighting module anchor is configured to provide hands-free and autonomously-modulated lighting to the caregiver in specific locations within the hospital where light is needed to perform care tasks; and wherein the proximity sensor system is configured to determine distance to the tag through ultra-wideband (UWB) telemetry;
   wherein the red-shifted light spectra reduces light in the 460-480 nanometer wavelength range; and
   wherein the lighting module anchor initiates illumination of the light emitter based on a distance between the proximity sensor system and the tag being 8 feet, and the lighting module anchor increases the light emitter to 100% intensity based on a distance being 1 foot or less.

2. The system of claim 1, wherein the lighting module anchor further comprises a sensor selected from the group consisting of a light sensor, a sound sensor, a vibration sensor, a rotation sensor, or combinations thereof.

3. The system of claim 1, wherein the lighting module anchor comprises a battery.

4. A method for providing circadian-friendly lighting for nighttime hospital care, the method comprising:
   providing a lighting module anchor that includes a body that encloses a proximity sensor system, a processor, a light emitter configured to emit red-shifted light spectra that reduces light in the 460-480 nanometer wavelength range, the body including a translucent portion that at least partially encloses the light emitter, the body further including a first type of hanger portion and a second type of hanger portion;
   hanging the lighting module anchor from a first type of mounting point in a first room of a first patient using the first type of hanger portion;
   hanging the lighting module anchor from a second type of mounting point in a second room of a second patient using the second type of hanger portion, wherein the second type of mounting point is a different type of mounting point than the first type of mounting point,
   at each mounting point, determining, by the lighting module anchor using the proximity sensor system and the processor, a distance to a tag communicative with the proximity sensor system through ultra-wideband (UWB) telemetry, the tag being coupled to a caregiver; and
   providing hands-free and autonomously-modulated lighting to the caregiver in specific locations within the hospital where light is needed to perform care tasks by modulating, by the lighting module anchor, light intensity of emitted light of the light emitter based on the distance between the proximity sensor system and the tag, including increasing the light intensity with closer proximity between the tag and the proximity sensor system, and decreasing the light intensity with increased distance therebetween; and
   wherein in performing the modulating, the lighting module anchor initiates the illumination based on the distance to the tag being 8 feet, and increases the intensity of illumination to 100% intensity based on the distance to the tag being 1 foot or less.

\* \* \* \* \*